United States Patent
Suzuki et al.

(10) Patent No.: US 8,157,732 B2
(45) Date of Patent: Apr. 17, 2012

(54) METHOD AND APPARATUS FOR MEASURING AUTONOMIC-NERVOUS INDEX AND APPARATUS FOR DETECTING BIOLOGICAL INFORMATION

(75) Inventors: Takuji Suzuki, Kanagawa (JP); Kenichi Kameyama, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1088 days.

(21) Appl. No.: 12/036,740

(22) Filed: Feb. 25, 2008

(65) Prior Publication Data

US 2008/0242956 A1   Oct. 2, 2008

(30) Foreign Application Priority Data

Mar. 27, 2007 (JP) ................. 2007-082621

(51) Int. Cl.
*A61B 5/00* (2006.01)
*A61B 5/0402* (2006.01)
(52) U.S. Cl. ....................................... 600/301; 600/509
(58) Field of Classification Search ........................ None
See application file for complete search history.

(56) References Cited

U.S. PATENT DOCUMENTS

| | | | |
|---|---|---|---|
| 2005/0234314 A1 | 10/2005 | Suzuki et al. | |
| 2006/0189855 A1 | 8/2006 | Moriya et al. | |
| 2007/0106183 A1 | 5/2007 | Suzuki et al. | |
| 2008/0004811 A1 | 1/2008 | Suzuki et al. | |

FOREIGN PATENT DOCUMENTS

| | | |
|---|---|---|
| JP | 7-143972 | 6/1995 |
| JP | 2002-291710 | 10/2002 |
| JP | 2003-265422 A | 9/2003 |
| JP | 2004-358022 A | 12/2004 |
| JP | 2005-124718 A | 5/2005 |
| JP | 2005-279113 A | 10/2005 |
| JP | 2006-212218 A | 8/2006 |
| JP | 2007-319233 A | 12/2007 |

OTHER PUBLICATIONS

U.S. Appl. No. 11/854,935, filed Sep. 13, 2007, Akihisa Moriya, et al.
U.S. Appl. No. 12/212,182, filed Sep. 17, 2008, Suzuki.

*Primary Examiner* — John S Brusca
(74) *Attorney, Agent, or Firm* — Oblon, Spivak, McClelland, Maier & Neustadt, L.L.P.

(57) ABSTRACT

A detection-rate calculating unit calculates a detection rate representing a ratio of number of interval data representing a time interval of one cycle of a waveform of at least one of a pulse and a heart rate, generated within a predetermined reference time to a sum of the number of the interval data and number of error data representing a content of an error occurred while the interval data is generated. When the detection rate is larger than the first threshold, an index calculating unit calculates an autonomic-nervous index representing an autonomic-nervous activity state, based on the interval data generated within the reference time.

14 Claims, 27 Drawing Sheets

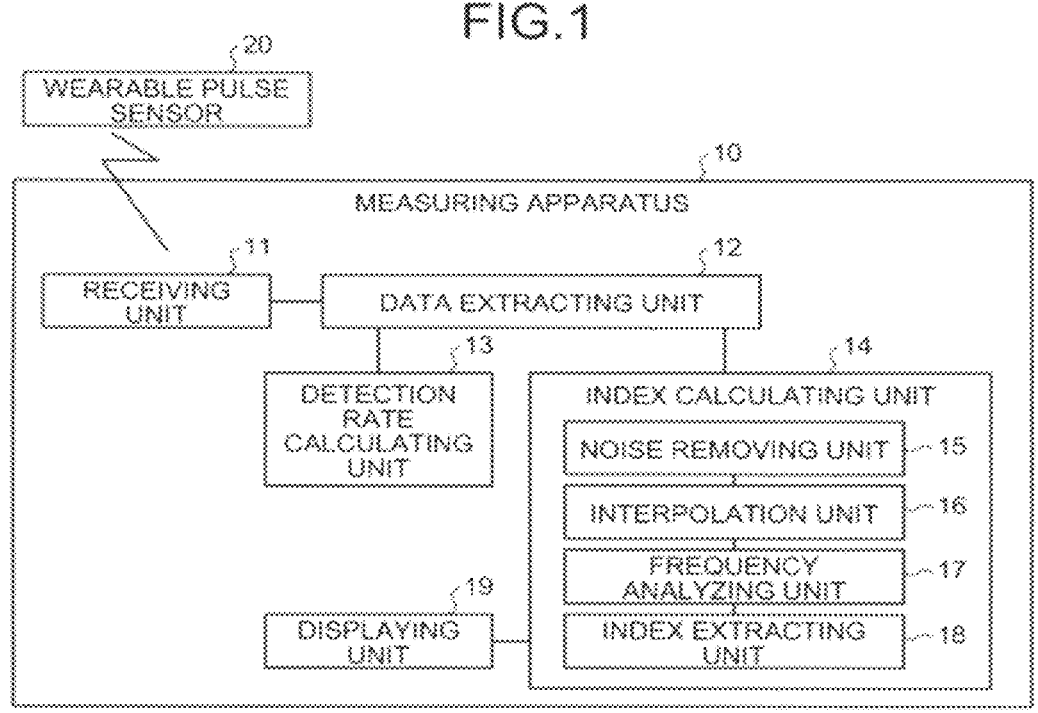

FIG.3

| | | | |
|---|---|---|---|
| N | 9.9147 | 0.9943 | |
| N | 11.052 | 1.1373 | |
| . | | | |
| . | | | |
| F | 50.8565 | | |
| G | 51.7264 | | |
| N | 59.5789 | 0.8589 | |
| M | 1 | 378 | 0.83 |
| N | 0.2698 | 0.7534 | |
| F | 0.6517 | | |
| N | 1.7325 | 1.0877 | |
| N | 2.5253 | 0.7928 | |
| . | | | |
| . | | | |
| N | 58.3582 | 0.5562 | |
| E | 59.8125 | | |
| M | 2 | 208 | 0.92 |
| E | 3.1875 | | |
| N | 4.4036 | 0.8411 | |
| N | 5.4133 | 1.0097 | |
| . | | | |
| . | | | |
| N | 59.2921 | 0.5675 | |
| M | 3 | 50 | 0.61 |
| N | 0.1041 | 0.8541 | |
| N | 1.3119 | 1.2078 | |

- DATA OF FIRST ONE MINUTE
- DATA OF SECOND ONE MINUTE
- DATA OF THIRD ONE MINUTE

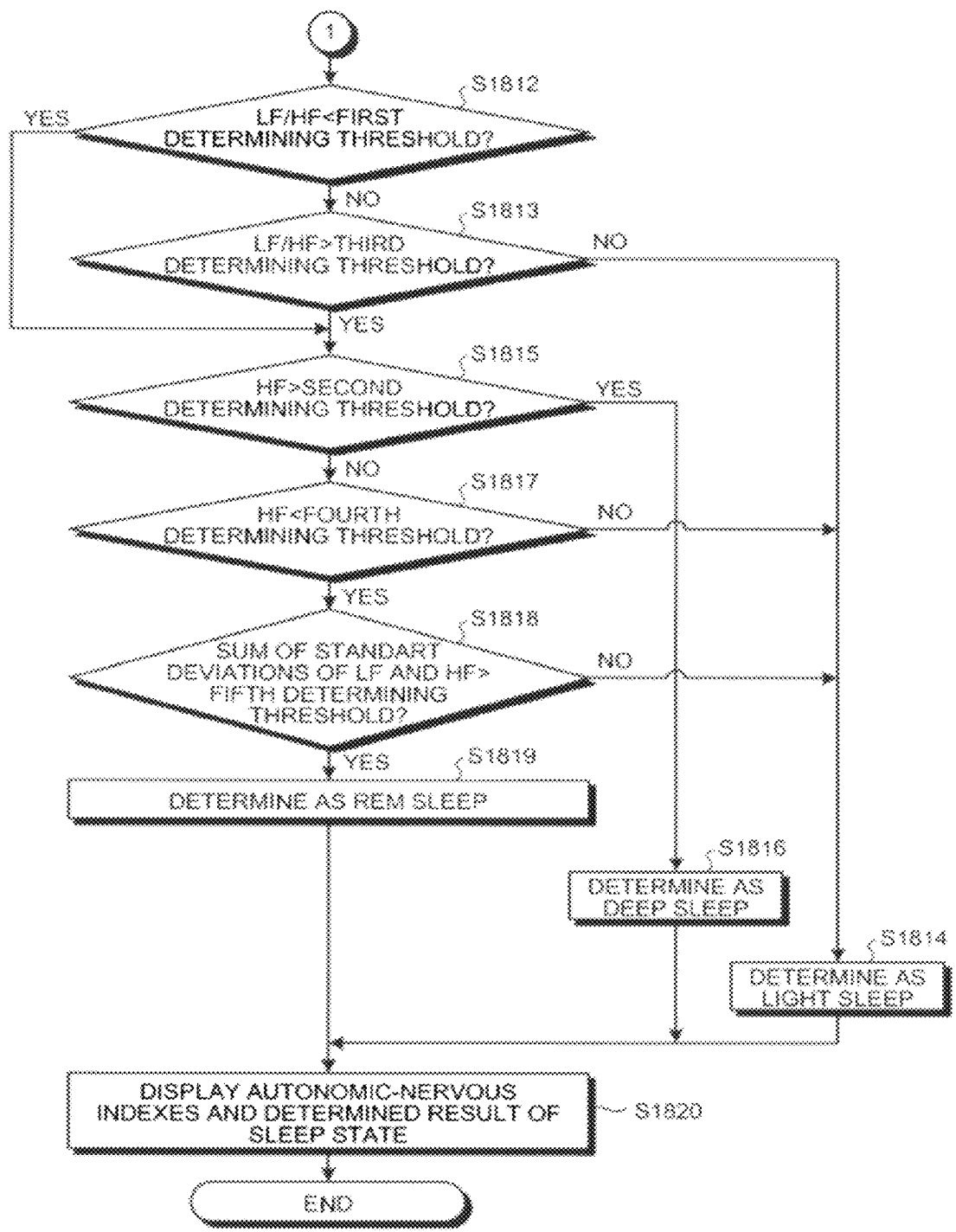

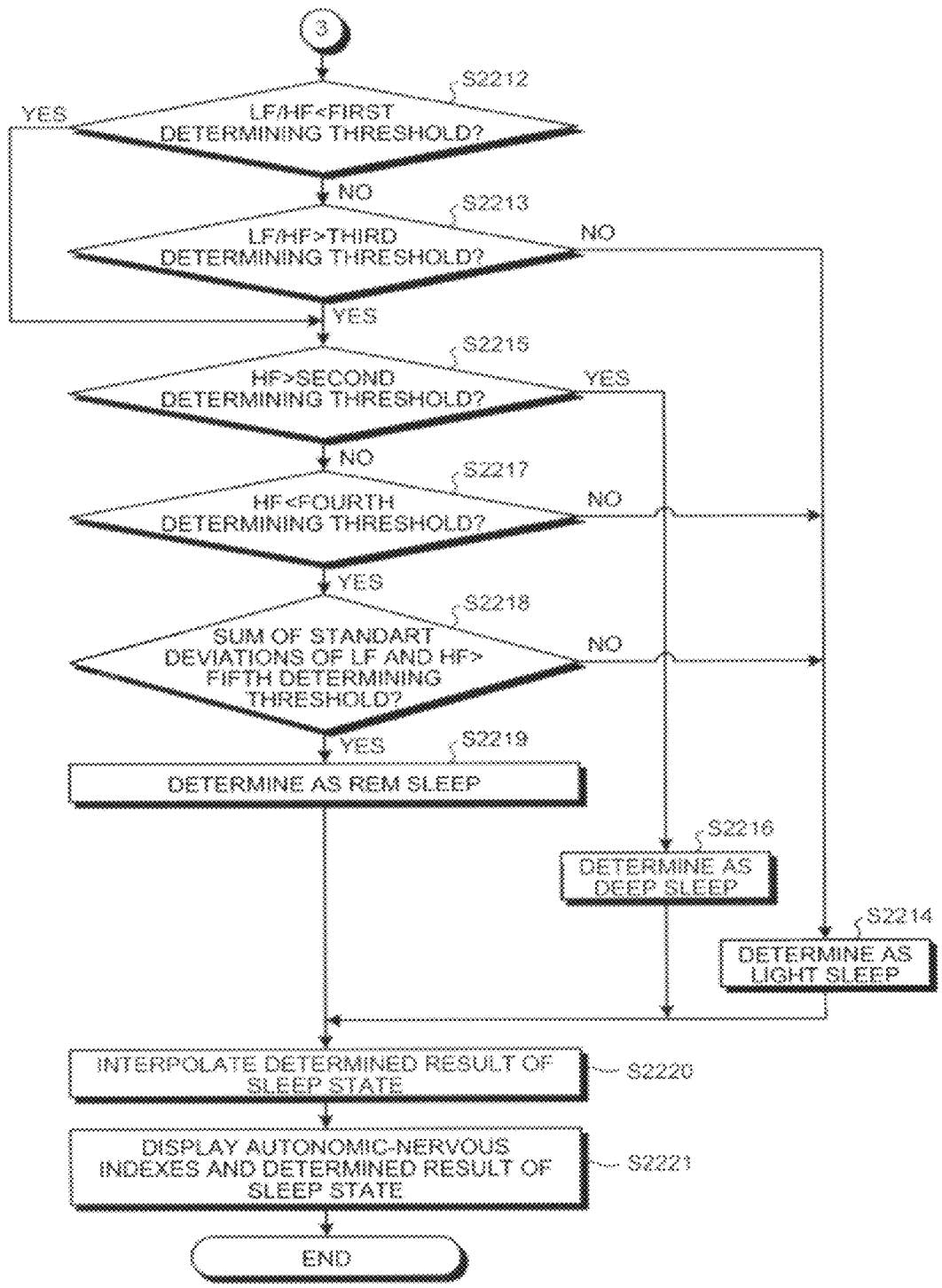

METHOD AND APPARATUS FOR MEASURING AUTONOMIC-NERVOUS INDEX AND APPARATUS FOR DETECTING BIOLOGICAL INFORMATION

CROSS-REFERENCE TO RELATED APPLICATIONS

This application is based upon and claims the benefit of priority from the prior Japanese Patent Application No. 2007-082621, filed on Mar. 27, 2007; the entire contents of which are incorporated herein by reference.

BACKGROUND OF THE INVENTION

1. Field of the Invention

The present invention relates to a method and an apparatus for measuring an autonomic-nervous index and an apparatus for detecting biological information.

2. Description of the Related Art

Generally, a polysomnogram for examination is used in medical institutions as a biological information monitoring apparatus that monitors biological information while a target person is in sleep. Apparatuses such as the polysomnogram are capable of monitoring various pieces of biological information such as electroencephalograms, electro-oculogram, and myogram, and determining a change in sleep state such as a rapid-eye-movement sleep (REM sleep) and a non-REM sleep based on the biological information monitored, and furthermore is capable of examining for disease during sleeping such as insomnia and apnea syndrome. However, because such apparatus is large in size, generally, it is used only in specialized institutions.

An apparatus for monitoring a sleep state or a health condition easily at home is developed. For example, JP-A 2002-291710 (KOKAI) and JP-A H07-143972 (KOKAI) disclose technologies in which a heartbeat interval of a heart rate that is an autonomic-nervous activity during sleeping is assumed as a pulse interval of a pulse wave, and a sleep state is determined according to an autonomic-nervous index obtained based on a variation of the pulse interval.

Because the pulse wave, which is a change in blood flow in a blood vessels of a palm, changes in synchronization with a heart rate, the heartbeat interval of the heart rate can be obtained based on the pulse interval of the pulse wave. In the methods disclosed in JP-A 2002-291710 (KOKAI) and JP-A H07-143972 (KOKAI), a series of pulse-interval data, which are monitored during sleeping with a portable biosensor such as a wristwatch type biosensor, are converted into a frequency spectrum distribution. Autonomic-nervous indexes are calculated from the power spectrums of a low-frequency band (LF: a band ranging from around 0.05 Hz to 0.15 Hz) and a high-frequency band (HF: a band ranging from around 0.15 Hz to 0.4 Hz) obtained from the pulse-interval data converted into the frequency spectrum distribution. Then, the sleep state is determined from the autonomic-nervous indexes obtained.

In a general autonomic-nervous analysis method, after the sensor stores raw data of the pulse wave, the raw data stored in the sensor is transferred to a Personal Computer (PC) for analysis, or the raw data sampled by the sensor is transferred to the PC in real time. Then, a pulse-interval detection and an autonomic-nervous analysis are performed on the raw data by an analysis software in the PC. In such a method, a sensor with higher performance is needed to ensure memory for storing the data in the sensor and ensure a communication capacity and a communication speed.

However, generally, a sensor with higher performance is large in size. Thus, using the sensor with higher performance is against the demand of improving a wearability of the sensor by downsizing the sensor. To solve this problem, the data, which is stored in the sensor or transferred to the PC, is compressed to reduce a necessary memory capacity and a communication load. Because only the pulse intervals are needed for monitoring the autonomic-nervous indexes and the sleep state, the data amount can be compressed by storing or transferring only the pulse-interval data, which has smaller capacity, through a pulse interval detecting process in the sensor.

Generally, a sensor that detects such biological information continues monitoring continuously during sleeping, and a monitoring accuracy is sometimes deteriorated due to a posture change of a target person during monitoring, a change in wearing state of the sensor with the posture change, and a temperature change. If raw data of the pulse wave is obtained, the deterioration of the monitoring accuracy is evaluated by analyzing the waveform characteristics.

However, in the method using the pulse-interval data, it is difficult to evaluate the monitoring accuracy, i.e., whether the pulse-interval data is correct. As described above, if raw data of the pulse wave is obtained, the deterioration of accuracy can be evaluated. However, because the advantage of the method of using the pulse-interval data is to utilize not the raw data but the compressed data, the raw data is normally not obtained.

SUMMARY OF THE INVENTION

An apparatus for measuring an autonomic-nervous index, according to one aspect of the present invention, includes a detection-rate calculating unit that calculates a detection rate representing a ratio of number of interval data generated within a predetermined reference time to a sum of the number of the interval data and number of error data generated within the reference time, the interval data representing a time interval of one cycle of a waveform of at least one of a pulse and a heart rate, the error data representing a content of an error occurred within the reference time; and an index calculating unit that calculates an autonomic-nervous index representing an autonomic-nervous activity state, based on the interval data generated within the reference time, when the detection rate is larger than the first threshold.

A method of measuring an autonomic-nervous index, according to another aspect of the present invention, includes calculating a detection rate representing a ratio of number of interval data generated within a predetermined reference time to a sum of the number of the interval data and number of error data generated within the reference time, the interval data representing a time interval of one cycle of a waveform of at least one of a pulse and a heart rate, the error data representing a content of an error occurred within the reference time; and calculating including comparing the detection rate with a predetermined first threshold, and calculating, when the detection rate is larger than the first threshold, an autonomic-nervous index representing an autonomic-nervous activity state, based on the interval data generated within the reference time.

A detecting device according to still another aspect of the present invention is configured to communicate with an apparatus that measures an autonomic-nervous index representing an autonomic-nerve activity state. The detecting device includes a detecting unit that detects a waveform of at least one of a pulse and a heart rate of a user; an analyzing unit that analyzes the at least one of the pulse and the heart rate of the user detected by the detecting unit, and generates an interval data representing a time interval of one cycle of the waveform of the at least one of the pulse and the heart rate and an error data representing a content of an error occurred when the interval data is generated; and a transmission unit that transmits the interval data and the error data to the apparatus.

BRIEF DESCRIPTION OF THE DRAWINGS

FIG. 1 is a block diagram of a measuring system according to a first embodiment of the present invention;

FIG. 2 is a table for explaining a data structure of an input data received by a wearable pulse sensor shown in FIG. 1;

FIG. 3 is an example of the input data;

FIGS. 18A and 18B are flowcharts of a sleep-state determining process;

DETAILED DESCRIPTION OF THE INVENTION

Figure 4:
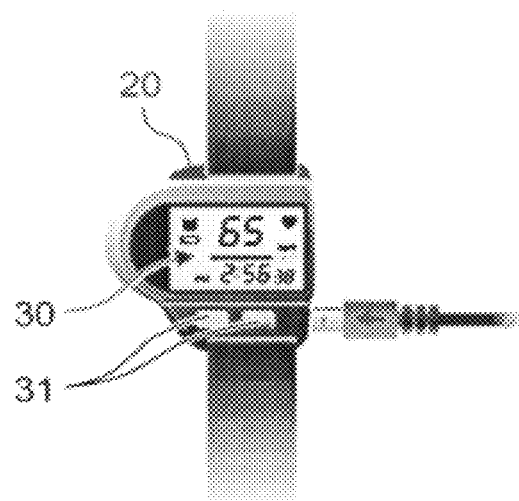
FIG. 4 is a top view of the wearable pulse sensor.

Exemplary embodiments of the present invention are explained in detail below with reference to the accompanying drawings.

In a measuring system according to a first embodiment of the present invention, a sensor that detects a pulse wave as biological information of a target person (user) calculates a pulse-interval data, and generates and stores an error data representing error contents during the calculation. Moreover, a measuring apparatus measures autonomic-nervous indexes by using the pulse-interval data and the error data received from the sensor. At this time, the measuring apparatus evaluates an accuracy of the pulse-interval data by using the error data, and measures the autonomic-nervous indexes by using the pulse-interval data with the accuracy more than a predetermined level.

As shown in FIG. 1, a measuring system 1 according to the first embodiment includes a measuring apparatus 10 that measures autonomic-nervous indexes and a wearable pulse sensor (hereinafter, "a pulse sensor") 20. The measuring apparatus 10 includes a receiving unit 11, a data extracting unit 12, a detection-rate calculating unit 13, an index calculating unit 14, and a displaying unit 19.

The receiving unit 11 receives an input data including a pulse-interval data and an error data by using a Universal Serial Bus (USB) communication function. The communication method is not limited to the USB, and any conventionally used communication methods including a short-distance wireless communication method with low-power consumption such as the Bluetooth can be employed.

In FIG. 2, for each type of the input data, a code for identifying the type of the input data, meaning of the code, and items (items 1 to 3) to be stored are related to one another.

For example, for a normal pulse-interval data, the code is set to N, and a detection time (sec) and a calculated pulse interval (sec) are input as the items. For a pulse-interval data out of the normal range (an out-of-range error), the code is set to E (instantaneous pulse rate calculated based on the pulse interval is 40 beats per minute (bpm) or less) or F (instantaneous pulse rate calculated based on the pulse interval is 110 bpm or more), and only the detection time is input. When a body movement is detected while detecting the pulse-interval data (a body-movement detected error), the code is set to G, and only the detection time is input. The instantaneous pulse rate (bpm) is calculated by dividing 60 sec by the pulse interval.

The input data whose code is set to E, F, or G is an error data, and each of the codes E, F, and G represents the contents of the error occurred during generation of the pulse-interval data. In addition to the input data (whose code is N, E, F, or G) that is output every time the pulse interval is calculated, the number of body movements and an average value of an amplitude of the pulse waveform in a predetermined time (e.g., one minute) are input as the data (a code M) calculated for every predetermined time.

As shown in FIG. 3, normally, after a plurality of input data, in each of which the code and the items 1 to 3 are related to one another, are output, the data of the code M is output as a data calculated every one minute.

The data extracting unit 12 extracts the pulse interval data and the error data from the received input data by determining the code. Specifically, the data extracting unit 12 extracts the data of the code N as the pulse-interval data and the data of the code E, F, or G as the error data.

The detection-rate calculating unit 13 counts the extracted pulse-interval data and error data, and calculates a detection rate. Specifically, the detection-rate calculating unit 13 first calculates the pulse-interval data and the error data every predetermined time (e.g., one minute). Then, the detection-rate calculating unit 13 calculates the ratio of the number of the pulse-interval data to the number of the total data received (excluding the data calculated every one minute) by the following equation:

$$DR = PI/TDR \quad (1)$$

where DR is detection rate, PI is the number of pulse-interval data, and TDR is the number of total data received. The number of total data received is obtained by adding the number of the pulse-interval data and the number of the error data.

The index calculating unit 14 calculates autonomic-nervous indexes when the detection rate is larger than a predetermined threshold. Furthermore, the index calculating unit 14 calculates the autonomic-nervous indexes when the number of the body movements is smaller than a predetermined number, and the pulse-wave amplitude is larger than a predetermined value. Thus, the index calculating unit 14 can evaluate the accuracy of the measured pulse-interval data, and does not calculate the autonomic-nervous indexes if the accuracy is low. The index calculating unit 14 includes a noise removing unit 15, an interpolation unit 16, a frequency analyzing unit 17, and an index extracting unit 18.

The noise removing unit 15 removes noise data from the pulse-interval data extracted by the data extracting unit 12. The interpolation unit 16 resamples the pulse-interval data with irregular intervals to data with regular intervals by a method such as a spline interpolation.

The frequency analyzing unit 17 performs frequency analysis on the resampled pulse-interval data by a method such as the Fast Fourier Transform (FFT), and converts the pulse-interval data subjected to the frequency analysis into a frequency area. The index extracting unit 18 extracts a low frequency (LF) area (a power of a LF component ranging from 0.05 Hz to 0.15 Hz) and a high frequency (HF) area (a power of a HF component ranging from 0.15 Hz to 0.4 Hz). The LF component and the HF component calculated in the above manner represent a sympathetic-nerous index and a parasympathetic-nerous index, respectively. The index calculating unit 14 calculates an LF/HF as an autonomic-nervous index besides the LF and the HF.

The displaying unit 19 displays the calculated autonomic-nervous indexes. The displaying unit 19 can be any conventional displaying unit.

Figure 5:
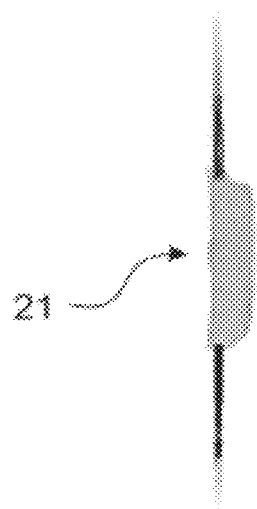
FIG. 5 is a side view of the wearable pulse sensor.

FIGS. 4 and 5 are each outline view of the pulse sensor 20. FIG. 4 is a top view of the pulse sensor 20, and FIG. 5 is a side view of the pulse sensor 20. As shown in FIGS. 4 and 5, the pulse sensor 20 is a wristwatch-type sensor to be attached to a wrist, and include a displaying unit 30 and an operating unit 31 on the top surface and a pulse-wave monitoring unit 21 that monitors a pulse wave of a target person on the bottom surface.

Figure 6:
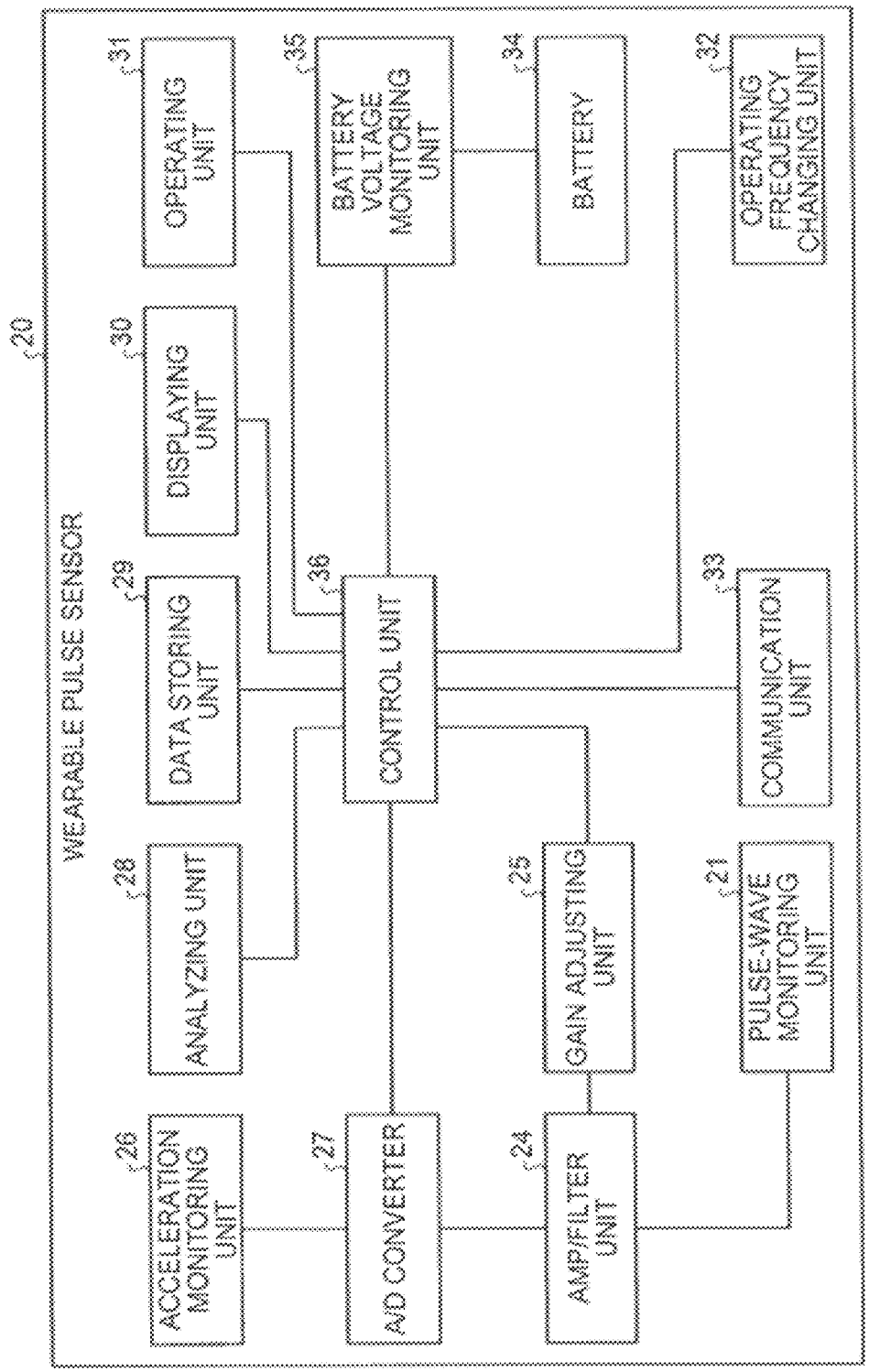
FIG. 6 is a block diagram of the wearable pulse sensor.

As shown in FIG. 6, the pulse sensor 20 includes the pulse-wave monitoring unit 21, an amp/filter unit 24, a gain adjusting unit 25, an acceleration monitoring unit 26, an Analog-to-Digital (A/D) converter 27, an analyzing unit 28, a data storing unit 29, the displaying unit 30, the operating unit 31, an operating-frequency changing unit 32, a communication unit 33, a battery 34, a battery-voltage monitoring unit 35, and a control unit 36.

As explained above by referring to FIG. 5, the pulse-wave monitoring unit 21 on bottom surface of the pulse sensor 20 monitors the pulse wave. The pulse-wave monitoring unit 21 includes a green light-emitting diode (LED) and a photo diode, and monitors fluctuation in a reflection light that changes according to the change in blood flow in a capillary vessel through radiation of light to a skin surface of a wrist by the photodiode.

The amp/filter unit 24 amplifies the monitored pulse waveform and performs filtering on it. Specifically, the amp/filter unit 24 converts an output current from the photodiode into a voltage by a current-voltage converter, amplifies the voltage by an amplifier, and performs a high-pass filtering (e.g., a cut-off frequency is 0.1 Hz) and a low-pass filtering (e.g., a cut-off frequency is 50 Hz).

The gain adjusting unit 25 adjusts a gain of the amp/filter unit 24 according to monitoring conditions. Specifically, the gain adjusting unit 25 calculates an amplitude of the pulse waveform input to the control unit 36, and controls the gain of the amp/filter unit 24 based on a relationship between the amplitude and a set threshold.

The acceleration monitoring unit 26 detects a dynamic acceleration generated with the movement of a wrist of a target person, and a static acceleration that is the gravity acceleration corresponding to the posture of the target person. Specifically, the acceleration monitoring unit 26 is an acceleration sensor that monitors acceleration in the range from −2 g to 2 g in three perpendicular directions, and is built in the pulse sensor 20.

The A/D converter 27 performs A/D conversion on the outputs from the pulse-wave monitoring unit 21 and the acceleration monitoring unit 26.

The analyzing unit 28 analyzes the data taken in by the A/D converter 27. Specifically, the analyzing unit 28 first analyzes the acceleration waveform that is obtained by monitoring acceleration by the acceleration monitoring unit 26 and performing A/D conversion on the acceleration by the A/D converter 27, and performs a body-movement-amount calculating process for calculating a body-movement-amount data of a target person. Then, the analyzing unit 28 performs a sleep-wake determining process determining whether the target person is in a wake state or in a sleep state by analyzing the calculated body-movement-amount data to calculate sleeping hours. Furthermore, the analyzing unit 28 analyzes the pulse waveform, which is obtained by monitoring a pulse wave by the pulse-wave monitoring unit 21, amplifying and performing filtering on the pulse wave by the amp/filter unit 24, and thereafter performing A/D conversion on the pulse wave by the A/D converter 27, and performs a pulse-interval calculating process for calculating a pulse-interval data.

Figure 7:
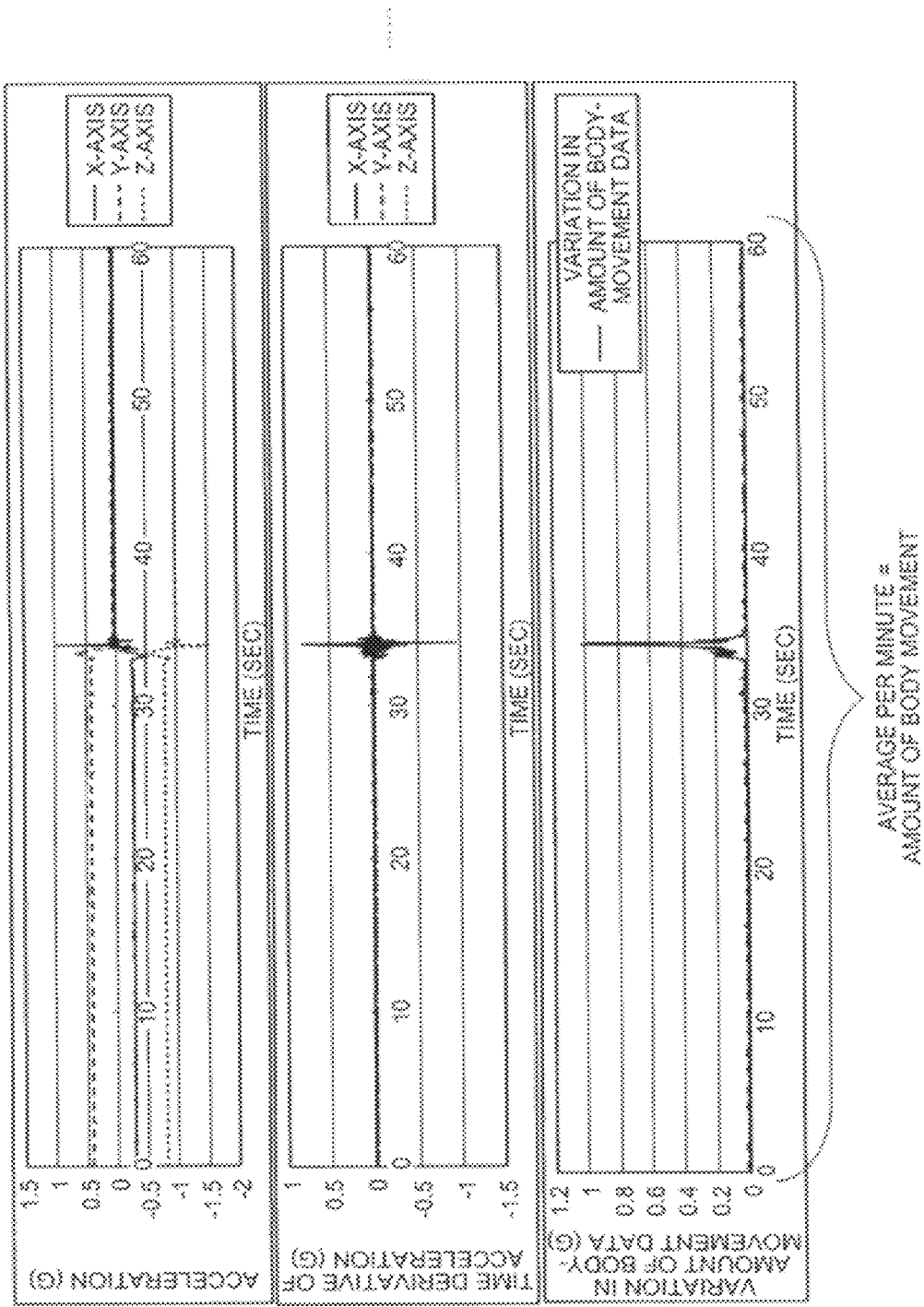
FIG. 7 is a graph of information obtained in a process of calculating an amount of body movement.

The body-movement-amount calculating process performed by the analyzing unit 28 is explained. The analyzing unit 28 first differentiates the acceleration data (in the upper graph in FIG. 7) in the three perpendicular directions obtained by the acceleration monitoring unit 26 with respect to time to calculate derivatives of the accelerations (in the middle graph in FIG. 7) in the three perpendicular directions. Then, the analyzing unit 28 calculates a variation in a body-movement data (in the lower graph in FIG. 7) that is a root-sum-square value of the derivatives of the acceleration in the three perpendicular directions. Finally, the analyzing unit 28 calculates a body-movement amount that is the average of the variation in the body-movement data in a predetermined time (e.g., one minute).

The sleep-wake determining process by the analyzing unit 28 is explained. The sleep-wake determining process is further divided into a body-movement determining process and a wake-state determining process.

In the body-movement determining process, the analyzing unit 28 determines a movement of the target person as the body movement when the variation in the body-movement data is larger than a body-movement threshold. The body-movement threshold is set to, for example, 0.01 G, which is the minimum value used in a body-movement measuring device.

In the wake-state determining process, when the frequency of the body movements determined in the body-movement determining process is equal to or larger than a frequency threshold, the analyzing unit 28 determines that the body movements have occurred during the wake state. When the frequency is under the frequency threshold, the analyzing unit 28 determines that the body movements have occurred during the sleep state. Furthermore, when the frequency is equal to or larger than the frequency threshold and the pulse interval is shorter than the average of past pulse intervals in the sleep state, the analyzing unit 28 determines that the body movements have occurred during the wake state. The frequency threshold is, for example, 5 times/minute based on past frequency data of the body movements in the wake state.

Figure 8:
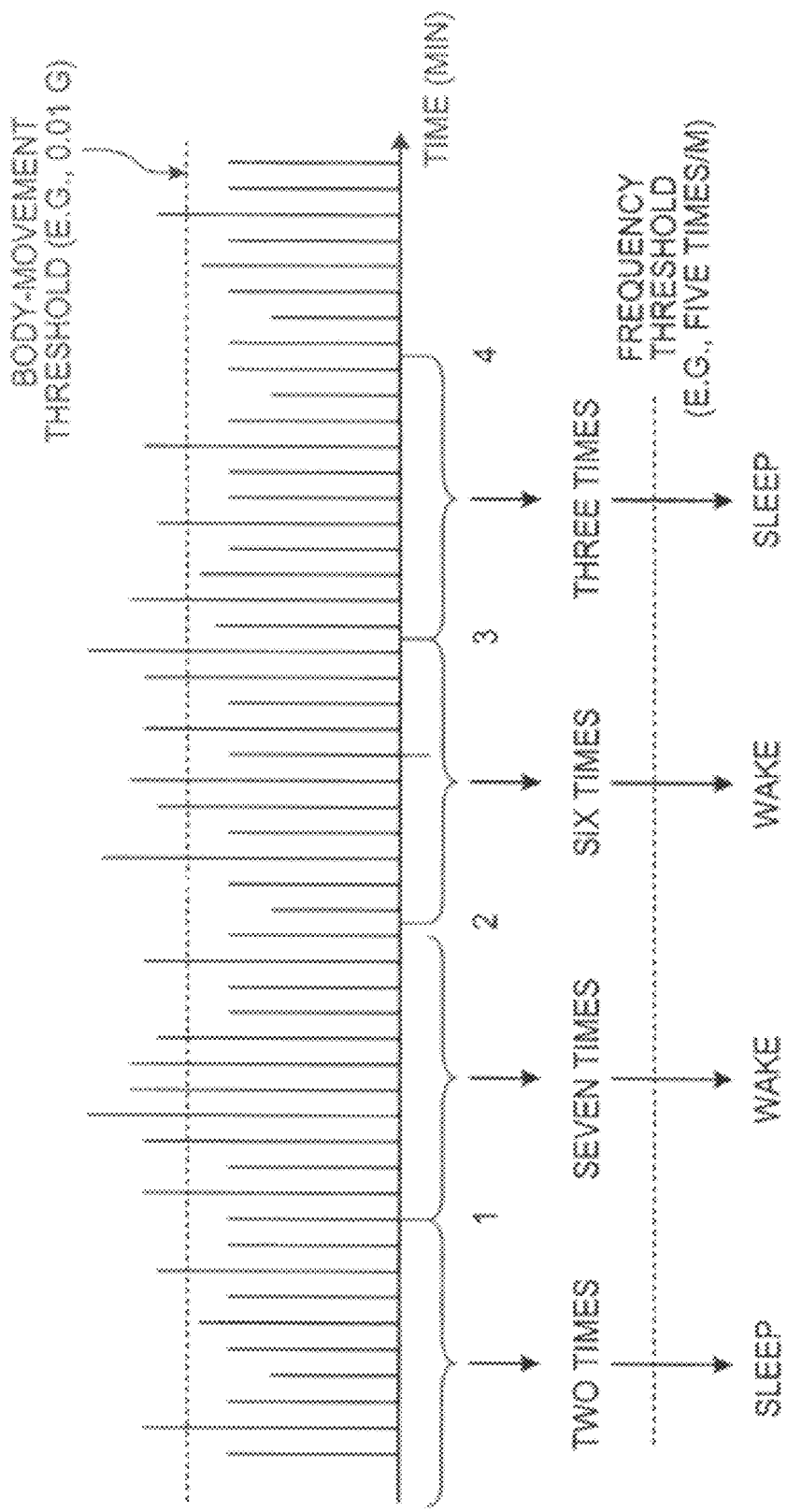
FIG. 8 is a schematic diagram for explaining a wake-state determining process.

In FIG. 8, for the four terms in which the number of the body movements over the body-movement threshold (0.01 G) is 2 times/minute, 7 times/minute, 6 times/minute, and 3 times/minute, respectively, the analyzing unit 28 determines that the body movements have occurred during the sleep state, the wake state, the wake state, and the sleep state, respectively, by comparing to the frequency threshold (5 times/minute).

From the result of the wake-sleep determining process, the time of transition from the wake state to the sleep state after starting the measurement is detected as a fall-asleep time, and the transition time from the wake state to the fall-asleep state when going back from the time when the measurement is finished is detected as a wake-up time. Sleeping hours are calculated according to the difference between the fall-asleep time and the wake-up time.

The data storing unit 29, which can be a flash memory, stores therein the monitored data such as a history of sleeping hours, the pulse-interval data, and the body-movement-amount data as the analysis result by the analyzing unit 28.

The displaying unit 30, which can be a liquid crystal display (LCD), displays the time, a pulse rate, a pulse-wave monitoring state, a battery state, a memory state, a communication state, and sleeping hours as the result.

The operating unit 31 includes a mode change-over switch between a time mode, a monitoring mode, and the like, and a push switch for turning on a back light. The operating-frequency changing unit 32 changes the operating frequency according to the mode set.

The communication unit 33 transmits and receives data to/from an external device. For example, the communication unit 33 transmits the data stored in the data storing unit 29 to the measuring apparatus 10.

The communication unit 33, which can be the USB, interacts with external devices such as a personal computer (PC) (not shown), a Personal Digital Assistants (PDA) terminal (not shown), or a cellular phone for data communications (not shown). The communication unit 33 makes it possible to, for example, monitor and store data during sleeping for a number of days, store the data with a format capable of being analyzed by a predetermined analysis software in the PC by connecting the PC to a USB port, and analyze the data by the analysis software.

The battery 34 supplies power to the pulse sensor 20, and the battery-voltage monitoring unit 35 monitors the voltage of the battery 34.

The control unit 36 controls the pulse sensor 20 based on the requests and the instructions received from the target person. For example, the control unit 36 controls operations such as power ON or OFF, and various processes related to the start of measuring and the measuring in response to the target person's instruction.

Figure 9:
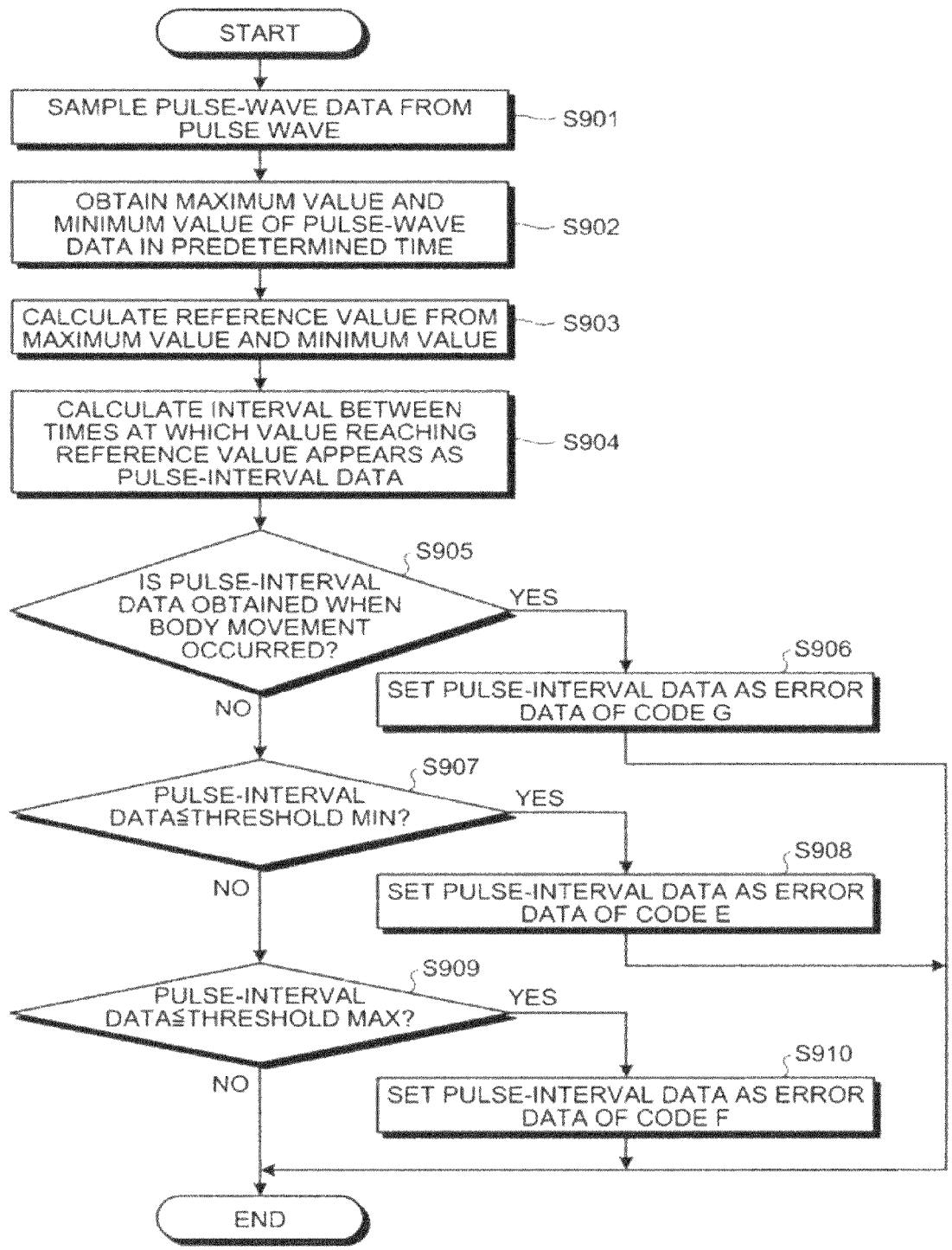
FIG. 9 is a flowchart of a pulse-interval calculating process.

The pulse-interval calculating process by the pulse sensor 20 according to the first embodiment is explained referring to FIG. 9.

First, the analyzing unit 28 samples a pulse-wave data from a pulse wave (step S901). Next, the analyzing unit 28 obtains the maximum and minimum values out of a series of the sampled pulse-wave data within about 2 sec centering on a process point of the pulse-wave data (step S902).

Next, the analyzing unit 28 calculates a reference value based on the maximum value and the minimum value (step S903). For example, the analyzing unit 28 calculates the difference between the maximum value and the minimum value as amplitude, and calculates a dividing point, which divides the calculated amplitude into 3:1, as the reference value. Next, the analyzing unit 28 calculates points of time when pulse-wave data reaches the reference value from the series of pulse-wave data with the direct-current variation components removed, and calculates the intervals between the points of time as the pulse-interval data (step S904). The analyzing unit 28 stores the calculated pulse-interval data in the data storing unit 29.

Figure 10:
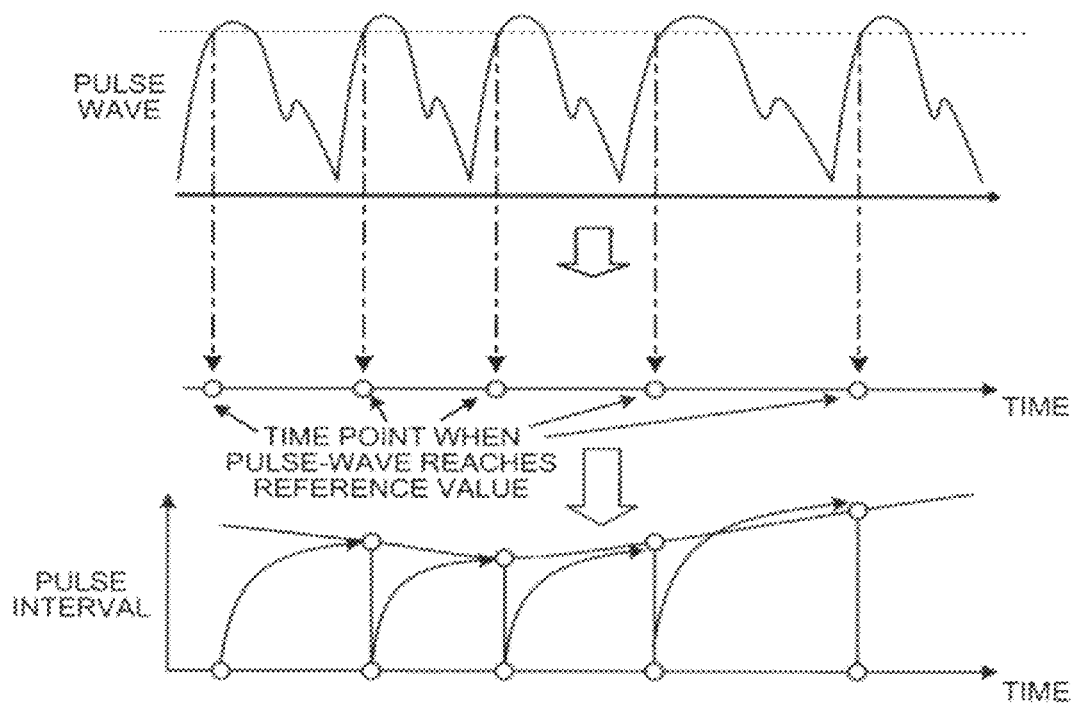
FIG. 10 is a schematic diagram for explaining calculation of a pulse-interval data.

FIG. 10 is a schematic diagram for explaining calculation of the pulse-interval data. Specifically, FIG. 10 depicts that points of time when the pulse-wave data (in the upper graph) reaches the reference value are obtained (in the middle graph), and the intervals of the calculated points of time are obtained as the pulse-interval data (in the lower graph).

The analyzing unit 28 determines whether the calculated pulse intervals are within the normal range in the following manner. That is, first, the analyzing unit 28 recognizes the occurrence of the body movement from the body-movement data at the time of detecting the pulse in the body-movement determining process, and determines whether the pulse-interval data is the data at the time of occurrence of the body movement (step S905).

When the pulse-interval data is the data at the time of occurrence of the body movement (Yes at step S905), the analyzing unit 28 sets the pulse-interval data as an error data of the code G as shown in FIG. 2 (step S906). When the pulse-interval data is not the data at the time of occurrence of the body movement (No at step S905), the analyzing unit 28 determines whether the pulse-interval data is equal to or smaller than a predetermined threshold MIN (e.g., 40 bpm), in which the value obtained by converting the pulse interval (sec) into the pulse rate (bpm) is compared with the threshold MIN (step S907).

When the pulse-wave interval is equal to or smaller than the threshold MIN (YES at step S907), the analyzing unit 28 determines the pulse-interval data as an error data of the code E (step S908). When the pulse-interval data is larger than the threshold MIN (NO at step S907), the analyzing unit 28 further determines whether the pulse-interval data is equal to or larger than a predetermined threshold MAX (e.g., 110 bpm) (step S909).

When the pulse-wave interval is equal to or larger than the threshold MAX (YES at step S909), the analyzing unit 28 determines the pulse-interval data as an error data of the code F (step S910). When the pulse-interval data is smaller than the threshold MAX (NO at step S909), or if the analyzing unit 28 already determines the pulse-interval data as the error data at S906, S908, or S910, the analyzing unit 28 finishes the pulse-interval calculating process.

The analyzing unit 28 calculates the number of the body movements in one minute and an average amplitude in one minute, and records them in the data storing unit 29 together with the pulse-interval data calculated in the above manner.

The data recorded in the data storing unit 29 is transmitted to the measuring apparatus 10 via the communication unit 33 in which the USB or the like is used. The autonomic-nervous indexes are calculated in the measuring apparatus 10 based on the data transmitted.

Figure 11:
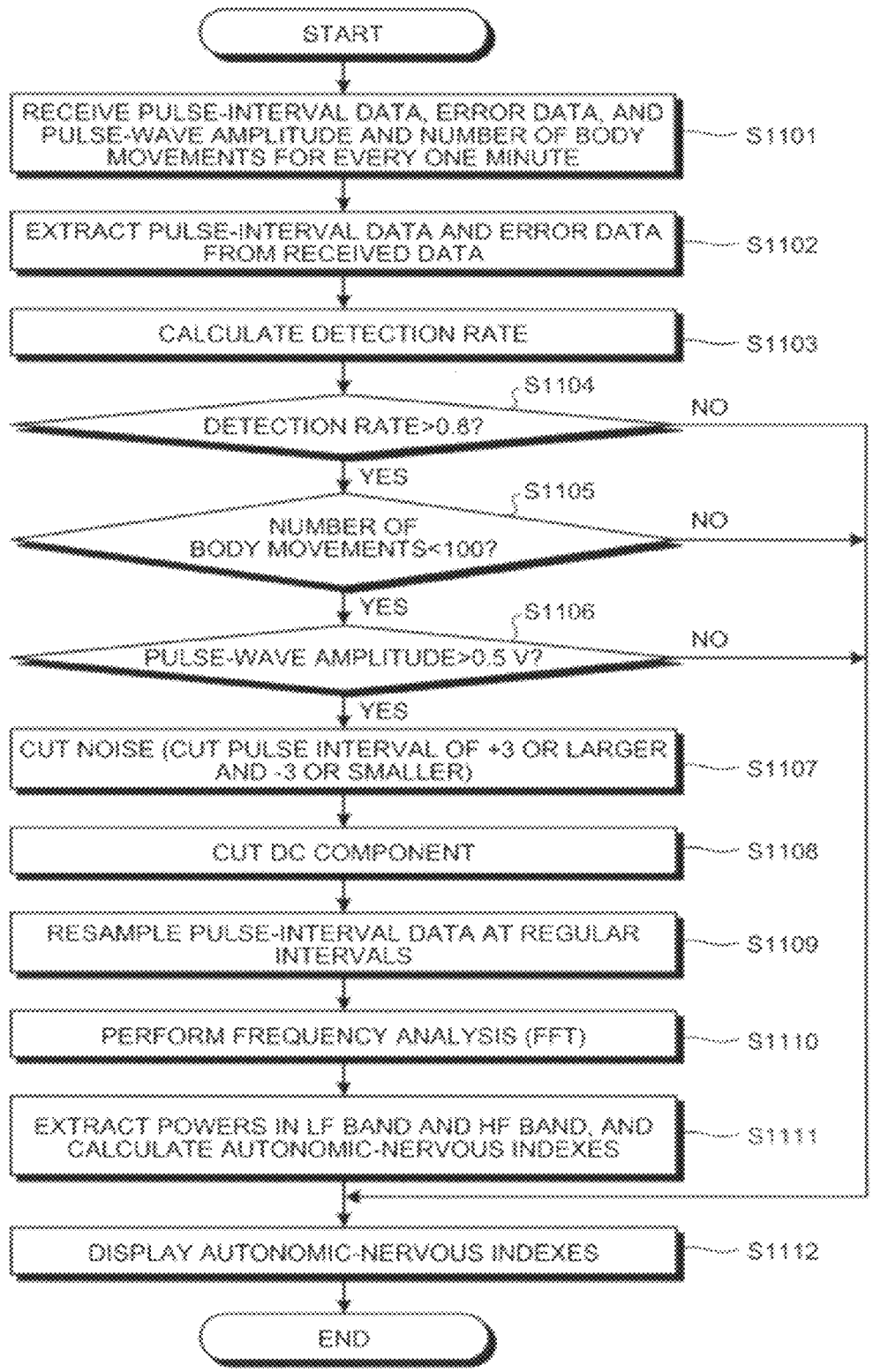
FIG. 11 is a flowchart of an index calculating process.

An index calculating process by the measuring apparatus 10 is explained referring to FIG. 11.

First, the receiving unit 11 receives an input data including the pulse-interval data, the error data, the pulse-wave amplitude in one minute, and the number of the body movements in one minute from the pulse sensor 20 (step S1101). Then, the data extracting unit 12 extracts the pulse-interval data and the error data from the input data received by determining the given codes (step S1102).

Next, the detection-rate calculating unit 13 calculates the detection rate from the extracted pulse-interval data and error data by the equation (1) (step S1103).

Next, the index calculating unit 14 determines whether the calculated detection rate is larger than a predetermined threshold (e.g., 0.8) (step S1104). When the detection rate is larger than the predetermined threshold (YES at step S1104), the index calculating unit 14 further determines whether the number of the body movements in one minute is smaller than a predetermined number (e.g., 100 times) (step S1105).

When the number of the body movements is smaller than the predetermined number (YES at step S1105), the index calculating unit 14 further determines whether the pulse-wave amplitude is larger than a predetermined value (e.g., an output voltage of 0.5 V) (step S1106).

When the pulse-wave amplitude is larger than the predetermined value (YES at step S1106), the index calculating unit 14 determines that the pulse-interval data is properly measured and calculates the autonomic-nervous indexes as follows.

First, the noise removing unit 15 calculates a standard deviation of the pulse-wave data in one minute and removes the data of +3σ or larger and −3σ or smaller (step S1107). Then, the noise removing unit 15 removes the direct-current components (step S1108).

Next, the interpolation unit 16 resamples the pulse-interval data to the data with even intervals by a spline interpolation (step S1109). Then, the frequency analyzing unit 17 performs a frequency-analysis (e.g., FFT) on the resampled pulse-interval data (step S1110).

Next, the index extracting unit 18 calculates the powers in a low frequency (LF) band and a high frequency (HF) band based on the frequency spectrum obtained by the frequency analysis as the autonomic-nervous indexes (step S1111).

When the detection rate is not larger than the threshold (NO at step S1104), the number of the body movements is not smaller than the predetermined number (NO at step S1105), and the pulse-wave amplitude is not larger than the predetermined value (NO at step S1106), the index extracting unit 18 does not calculate the autonomic-nervous indexes.

Figure 12:
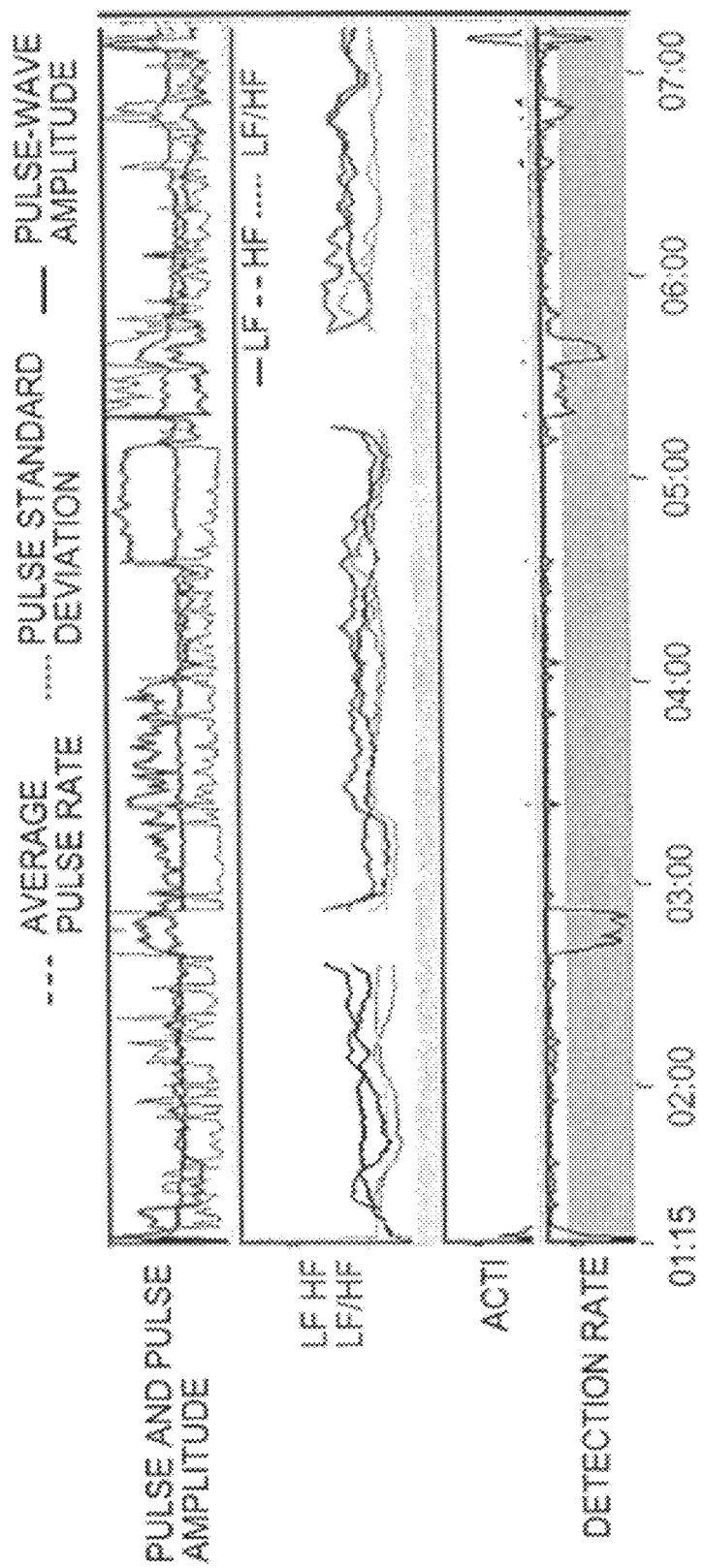
FIG. 12 is a graph representing an analysis result displayed on a displaying unit.

The autonomic-nervous indexes calculated are displayed on the displaying unit 19 (step S1112). FIG. 12 depicts an example in which a LF, a HF, and a LF/HF are displayed on the displaying unit 19 as the autonomic-nervous indexes. The autonomic-nervous indexes are not displayed for a time period in which the autonomic-nervous indexes are not calculated.

FIG. 11 is a flowchart of the index calculating process in which data is received and the autonomic-nervous indexes are calculated based on the data every predetermined time (one minute), and every time the autonomic-nervous indexes are calculated, the calculated autonomic-nervous indexes are displayed on the displaying unit 19. The autonomic-nervous indexes can be calculated and displayed at any timing. For example, the autonomic-nervous indexes can be calculated after receiving the data recorded in the pulse sensor 20 in a lump sum, or the analysis results can be displayed on the displaying unit 19 after analyzing all data.

According to the first embodiment, as shown in FIG. 12, the autonomic-nervous indexes are not displayed for the time period in which the detection rate is determined to be smaller than the predetermined threshold due to deterioration of measuring accuracy.

Figure 13:
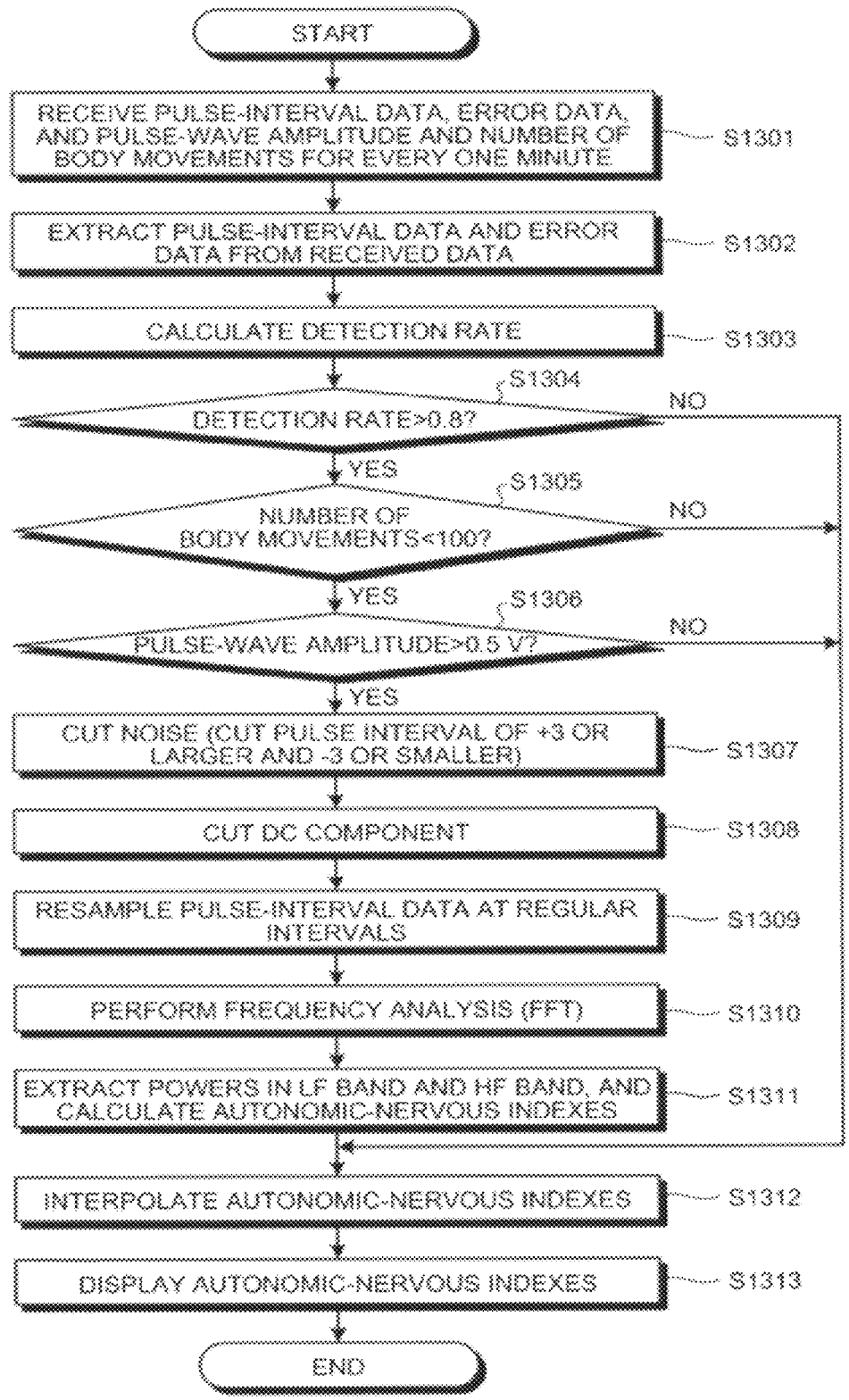
FIG. 13 is a flowchart of an index calculating process according to a first modification of the first embodiment.

In a first modification of the first embodiment, the autonomic-nervous indexes are calculated even for the time period in which the autonomic-nervous indexes are not calculated by interpolation using the autonomic-nervous indexes before and after the time period. As shown in FIG. 13, a process of interpolating the autonomic-nervous indexes (step S1312) is added before displaying the autonomic-nervous indexes. In such case, any conventional interpolation method such as a linear interpolation and a polynomial approximation technique (e.g., a cubic spline interpolation) that uses two points before and after the time period can be employed. Other steps are the same as those in FIG. 11, so that the explanation thereof is omitted.

Figure 14:
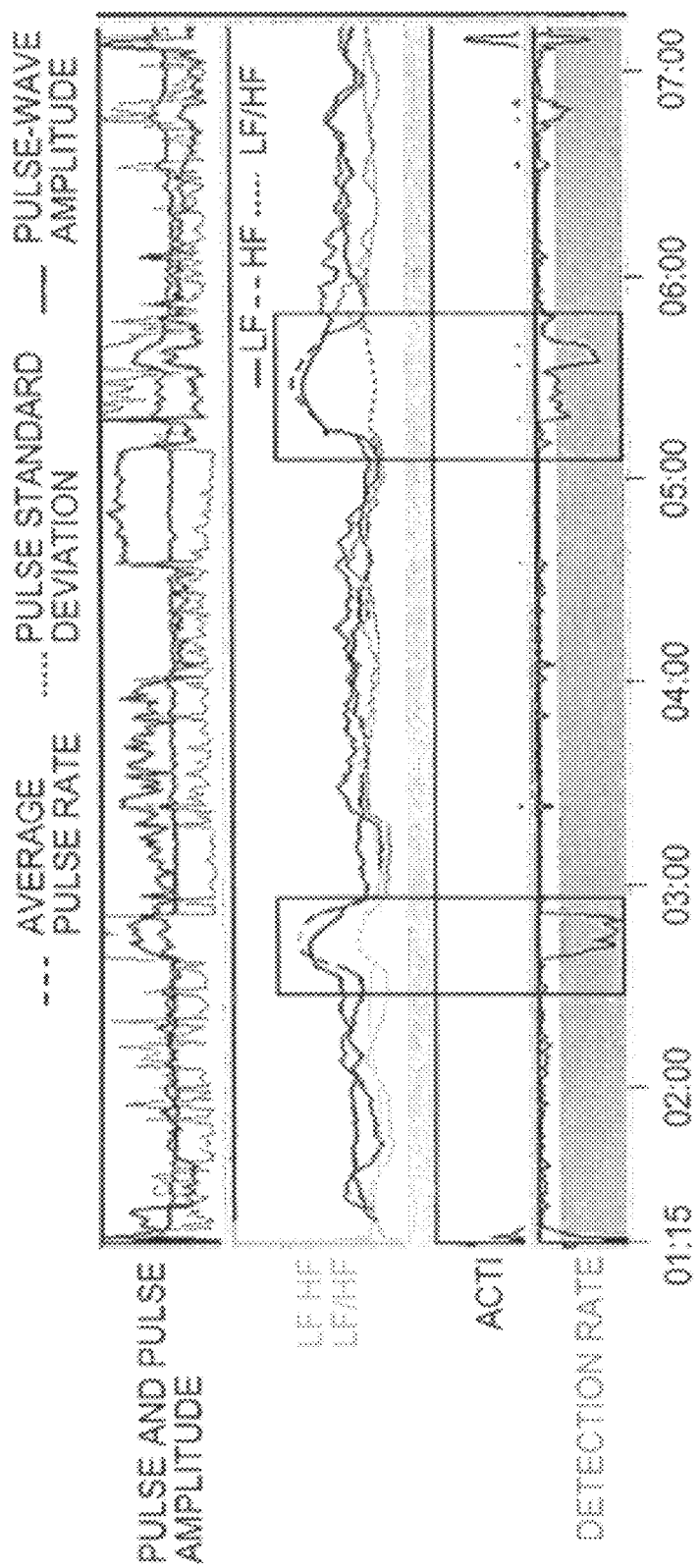
FIG. 14 is a graph representing an analysis result displayed on a displaying unit, the analysis result including autonomic-nervous indexes interpolated in the first modification.

As is apparent from the areas surrounded by the frames in FIG. 14, even when the detection rate is smaller than the predetermined threshold, the autonomic-nervous indexes interpolated by using the autonomic-nervous indexes before and after the time period are displayed on the displaying unit 19.

In the first embodiment, the pulse-interval data is calculated in the pulse sensor 20, however, the pulse sensor 20 can receive the pulse-wave data and the pulse-interval data can be calculated in the measuring apparatus 10.

Figure 15:
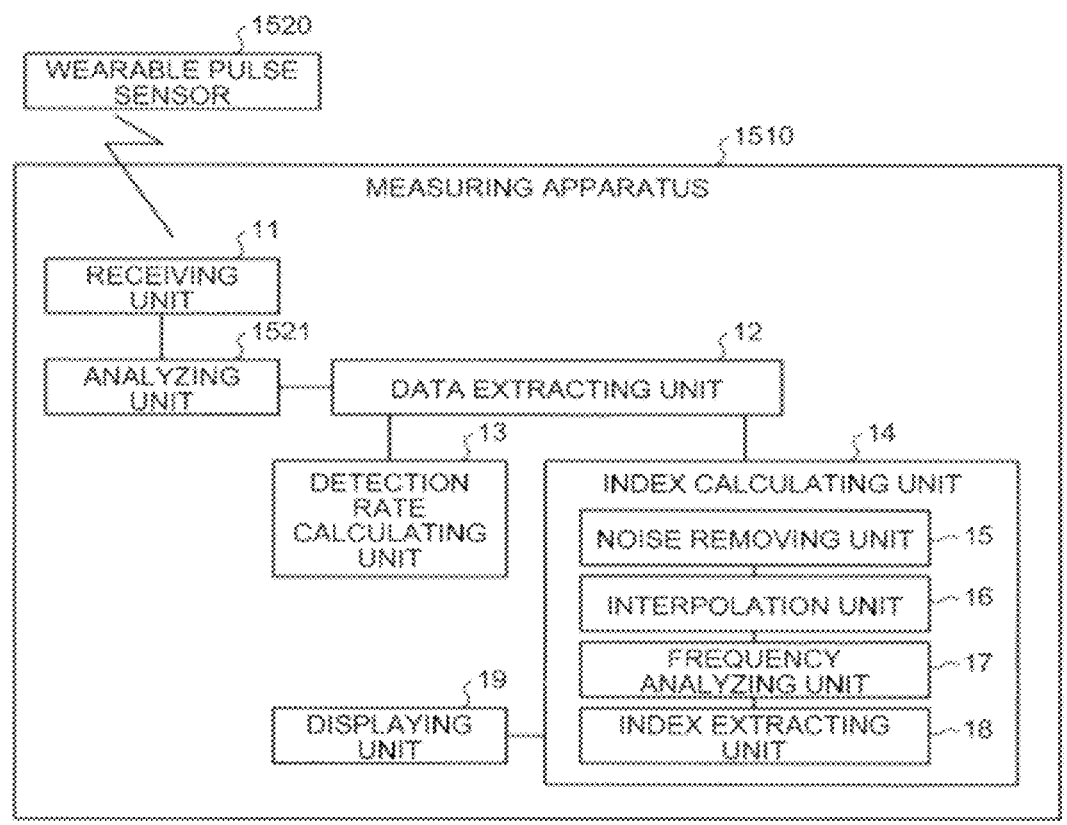
FIG. 15 is a block diagram of a measuring system according to a second modification of the first embodiment.

As shown in FIG. 15, a measuring apparatus 1510 of the measuring system according to a second modification includes an analyzing unit 1521 that analyzes the pulse-wave data received from the receiving unit 11. The analyzing unit 1521 works same as the analyzing unit 28 of the pulse sensor 20 in the first embodiment, so that the explanation thereof is omitted.

Figure 16:
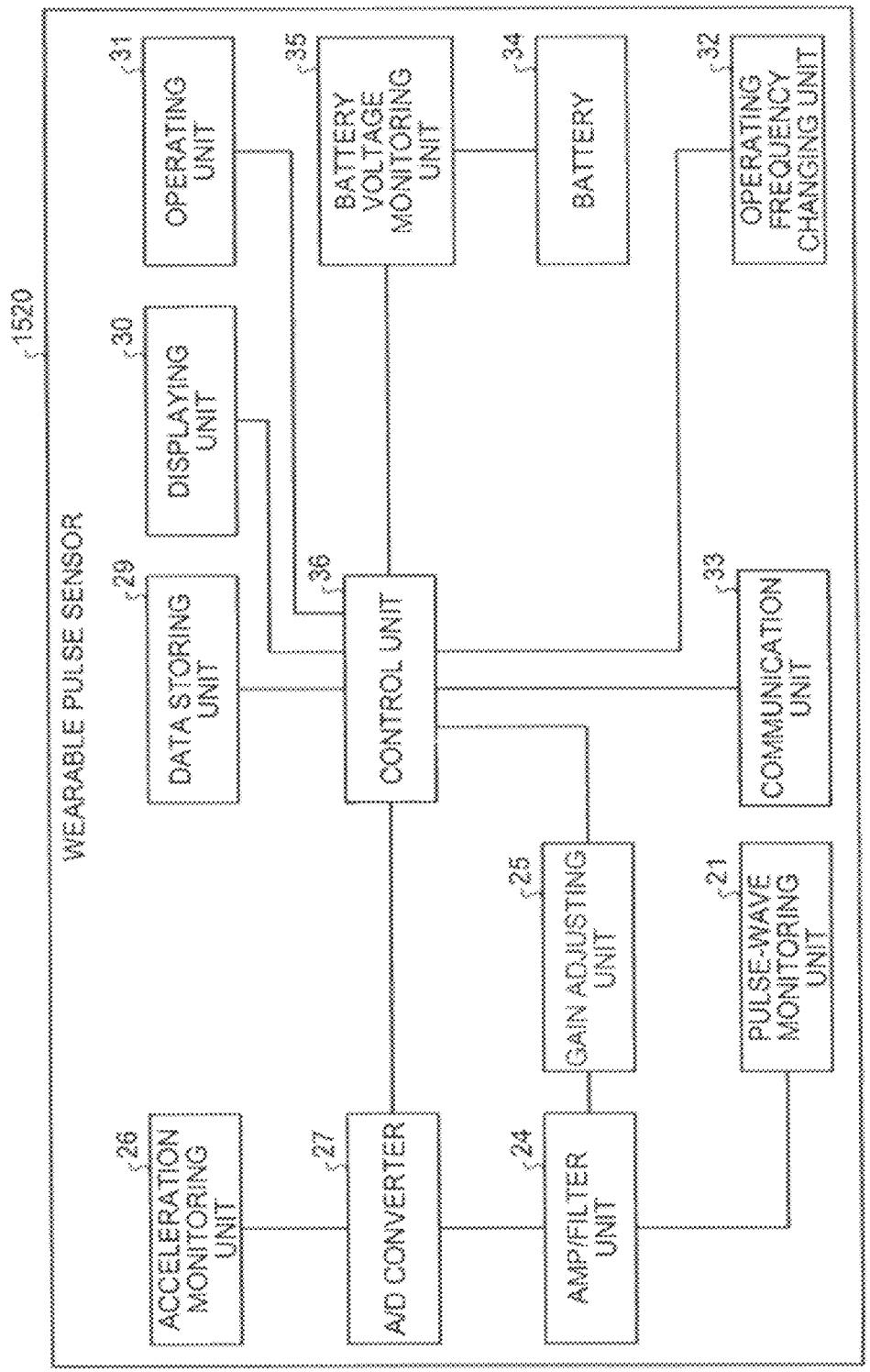
FIG. 16 is a block diagram of a wearable pulse sensor shown in FIG. 15.

As shown in FIG. 16, a wearable pulse sensor 1520 in a second modification is different from the pulse sensor 20 in the first embodiment, in which the analyzing unit 28 is not provided.

In other words, the pulse sensor 1520 does not perform the analyzing process, and stores the measured pulse-wave data in the data storing unit 29 and transmits it to the measuring apparatus 1510. Even with such configuration, the pulse-interval data can be calculated and the error data can be determined, so that the accuracy of the pulse-interval data can be evaluated.

In the above explanation, the pulse sensor that detects a pulse wave is used, however, an electrocardiographic sensor can be used and an electrocardiographic waveform monitored by the electrocardiographic sensor can be used. Even in such configuration, the same effect as that in the first embodiment can be obtained.

According to the first embodiment, the pulse-interval data is calculated and the error data representing the contents of the error at the time of calculation of the pulse-interval data is generated, and the accuracy of the pulse-interval data is evaluated by using the pulse-interval data and the error data, thus enabling to measure the autonomic-nervous indexes by using the pulse-interval data with accuracy above a predetermined level. Therefore, even when the autonomic-nervous indexes are calculated based on the pulse-interval data containing a small amount of information, the accuracy of the measured pulse-interval data can be evaluated, so that the biological information can be monitored with high accuracy. Moreover, it is possible to downsize the sensor and ensure the measuring accuracy.

A sleep-state determining apparatus 1710 according to a second embodiment further determines a sleep state by using the calculated autonomic-nervous indexes.

Figure 17:
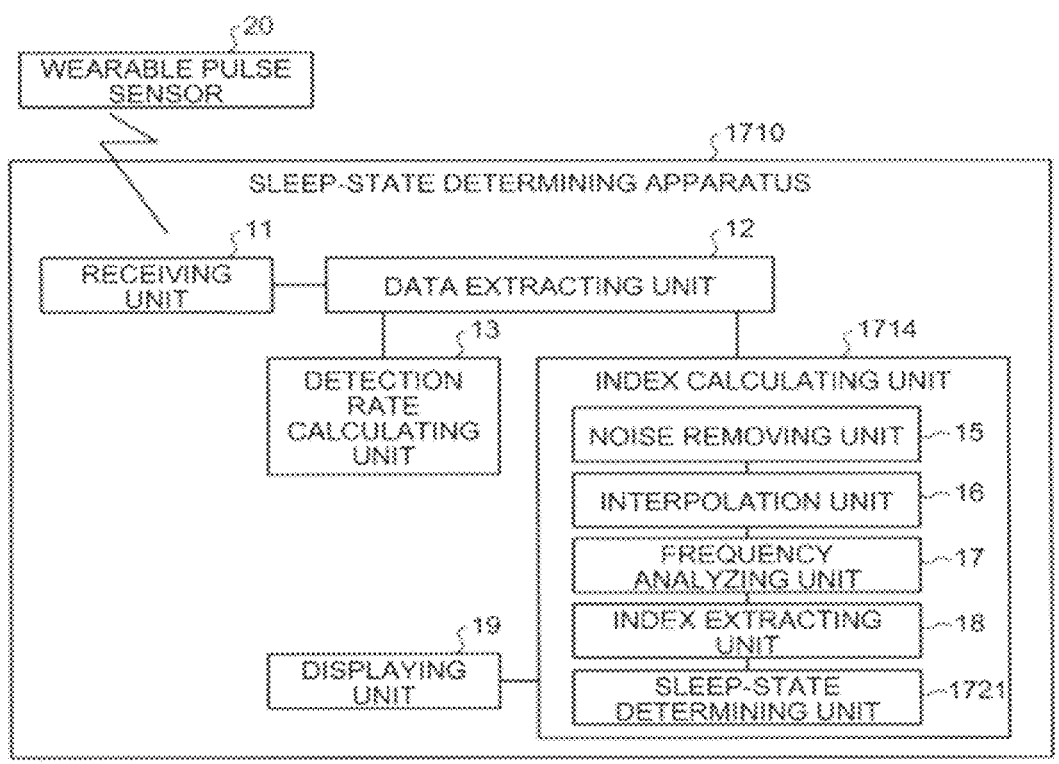
FIG. 17 is a block diagram of a sleep-state determining apparatus according to a second embodiment of the present invention.

As shown in FIG. 17, the sleep-state determining apparatus 1710 includes the receiving unit 11, the data extracting unit 12, the detection-rate calculating unit 13, an index calculating unit 1714, and the displaying unit 19.

In the second embodiment, constructions and functions of the components are the same as those in the first embodiment except the function of the index calculating unit 1714, so that the same components are given the same reference numerals, and the explanation thereof is omitted.

The index calculating unit 1714 calculates the autonomic-nervous indexes, and determines the sleep state of a target person by using the calculated autonomic-nervous indexes. The index calculating unit 1714 includes the noise removing unit 15, the interpolation unit 16, the frequency analyzing unit 17, the index extracting unit 18, and a sleep-state determining unit 1721.

The constructions and functions of the noise removing unit 15, the interpolation unit 16, the frequency analyzing unit 17, and the index extracting unit 18 are the same as those in the first embodiment, so that the explanation thereof is omitted.

The sleep-state determining unit 1721 compares the autonomic-nervous indexes LF/HF and HF with determining thresholds that are set in advance, thereby determining the sleep state that includes the stages of a REM sleep, a light sleep, and a deep sleep.

Figure 18A:
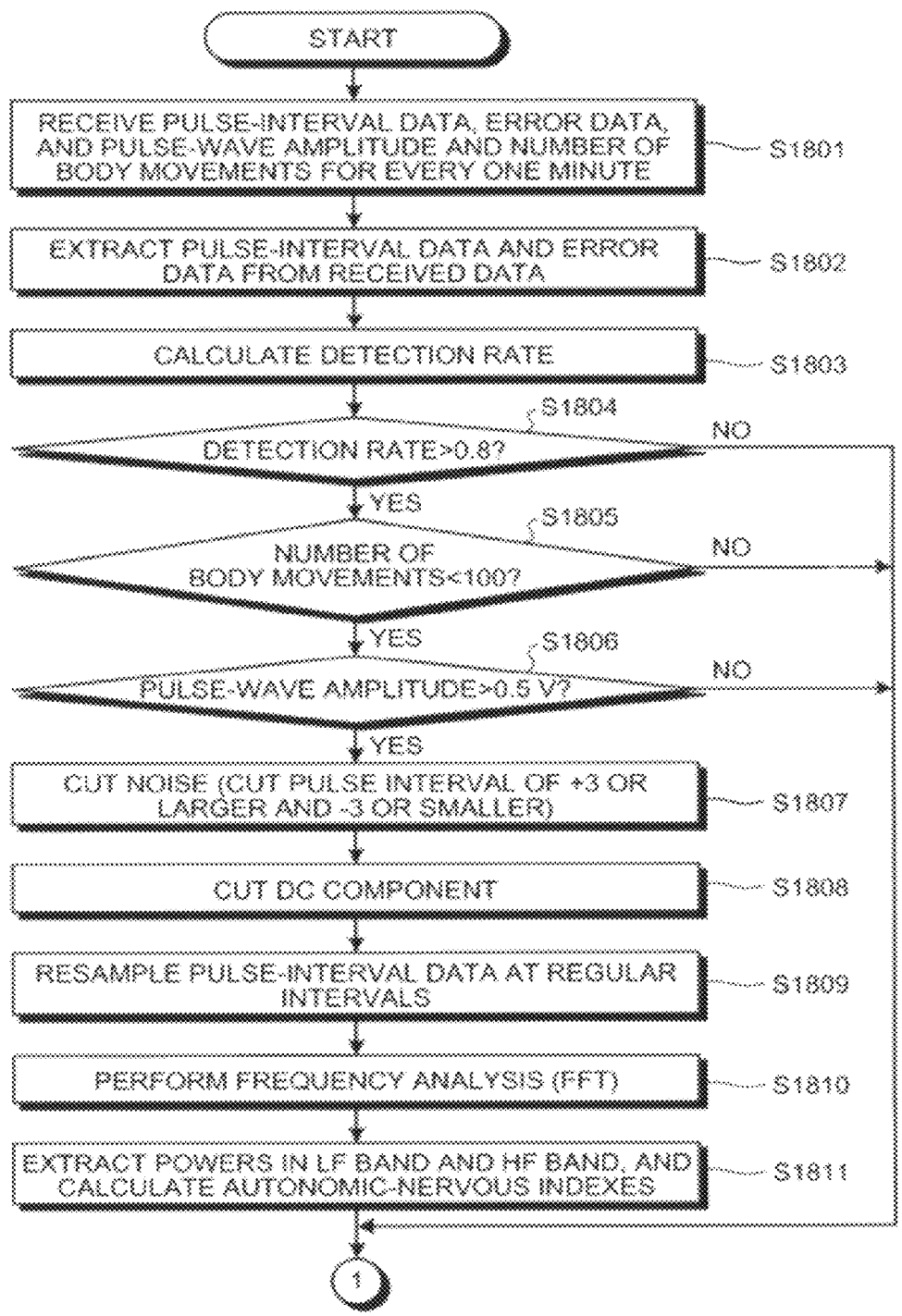

A sleep-state determining process by the sleep-state determining apparatus 1710 is explained referring to FIGS. 18A and 18B.

An autonomic-nervous-index measuring process from step S1801 to step S1811 is the same as that from step S1101 to step S1111 in the first embodiment, so that the explanation thereof is omitted.

After the autonomic-nervous indexes are calculated (step S1811), the sleep-state determining unit 1721 determines whether the LF/HF is smaller than a first threshold (step S1812). When the LF/HF is smaller than the first threshold (YES at step S1812), the sleep-state determining unit 1721 further determines whether the HF is larger than a second determining threshold (step S1815). When the HF is larger than the second determining threshold (YES at step S1815), the sleep-state determining unit 1721 determines the sleep state as the deep sleep (step S1816).

When the LF/HF is not smaller than the first determining threshold (NO at step S1812), the sleep-state determining unit 1721 further determines whether the LF/HF is larger than a third determining threshold (step S1813). When the LF/HF is larger than the third determining threshold (YES at step S1813), the sleep-state determining unit 1721 further determines whether the HF is larger than the second determining threshold (step S1815).

When the HF is not larger than the second determining threshold (NO at step S1815), the sleep-state determining unit 1721 further determines whether the HF is smaller than a fourth determining threshold (step S1817). When the HF is smaller than the fourth determining threshold (YES at step S1817), the sleep-state determining unit 1721 further determines whether the sum of the standard deviations of the LF and the HF is larger than a fifth determining threshold (step S1818). When the sum of the standard deviations of the LF and the HF is larger than the fifth determining threshold (YES at step S1818), the sleep-state determining unit 1721 determines the sleep state as the REM sleep (step S1819).

When the LF/HF is not larger than the third determining threshold (NO at step S1813), the HF is not smaller than the fourth determining threshold (NO at step S1817), or the sum of the standard deviations of the LF and HF is not larger than the fifth determining threshold (NO at step S1818), the sleep-state determining unit 1721 determines the sleep state as the light sleep (step S1814).

The first to fifth determining thresholds can be set, for example, as follows. That is, the LF, HF, LF/HF are monitored for each target person overnight, and two points having a high distribution density are selected for each of the LF, HF, LF/HF. Then, a midpoint between the two selected points of the LF/HF is set as the first determining threshold and the third determining threshold, a midpoint between the two selected points of the HF is set as the second determining threshold and the fourth determining threshold, and a midpoint between the two selected points of the LF is set as the fifth determining threshold.

The result of the sleep state determined in such manner is displayed on the displaying unit 19 together with the autonomic-nervous indexes (step S1820).

Figure 19:
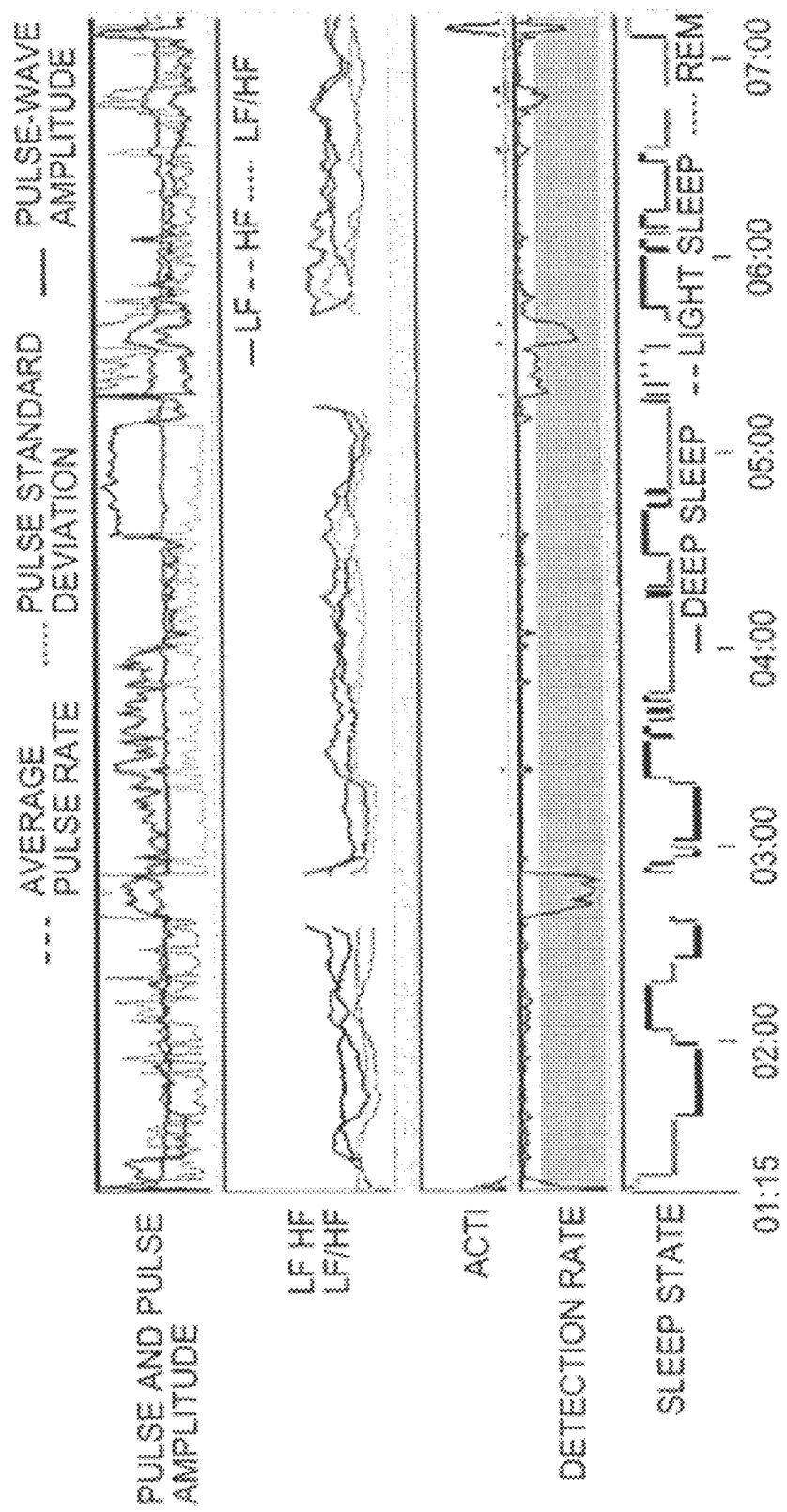
FIG. 19 is a graph representing a determined result of a sleep state displayed on a displaying unit.

For a time period that is determined to have a detection rate smaller than the predetermined threshold due to the deterioration of the measuring accuracy, the sleep state is not determined because the autonomic-nervous indexes are not calculated. Thus, as shown in FIG. 19, the autonomic-nervous indexes and the determined result of the sleep state are not displayed on the screen for the time period.

In a modification of the second embodiment, the sleep state of the time period in which the autonomic-nervous indexes are not calculated is determined by using the autonomic-nervous indexes that are interpolated from the autonomic-nervous indexes calculated before and after the time period.

Figure 20A:
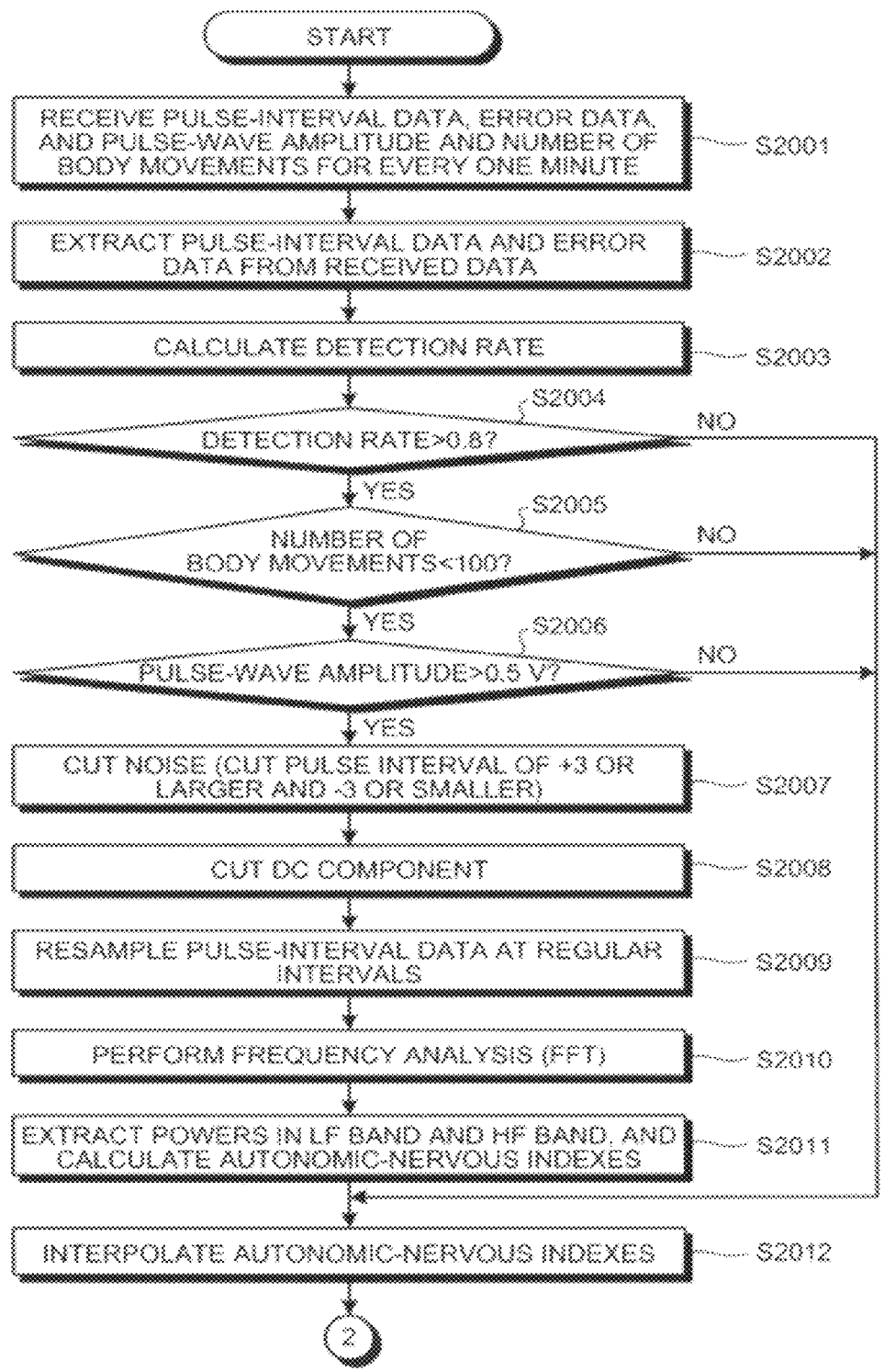
FIGS. 20A and 20B are flowcharts of a sleep-state determining process according to a first modification of the second embodiment.
Figure 20B:
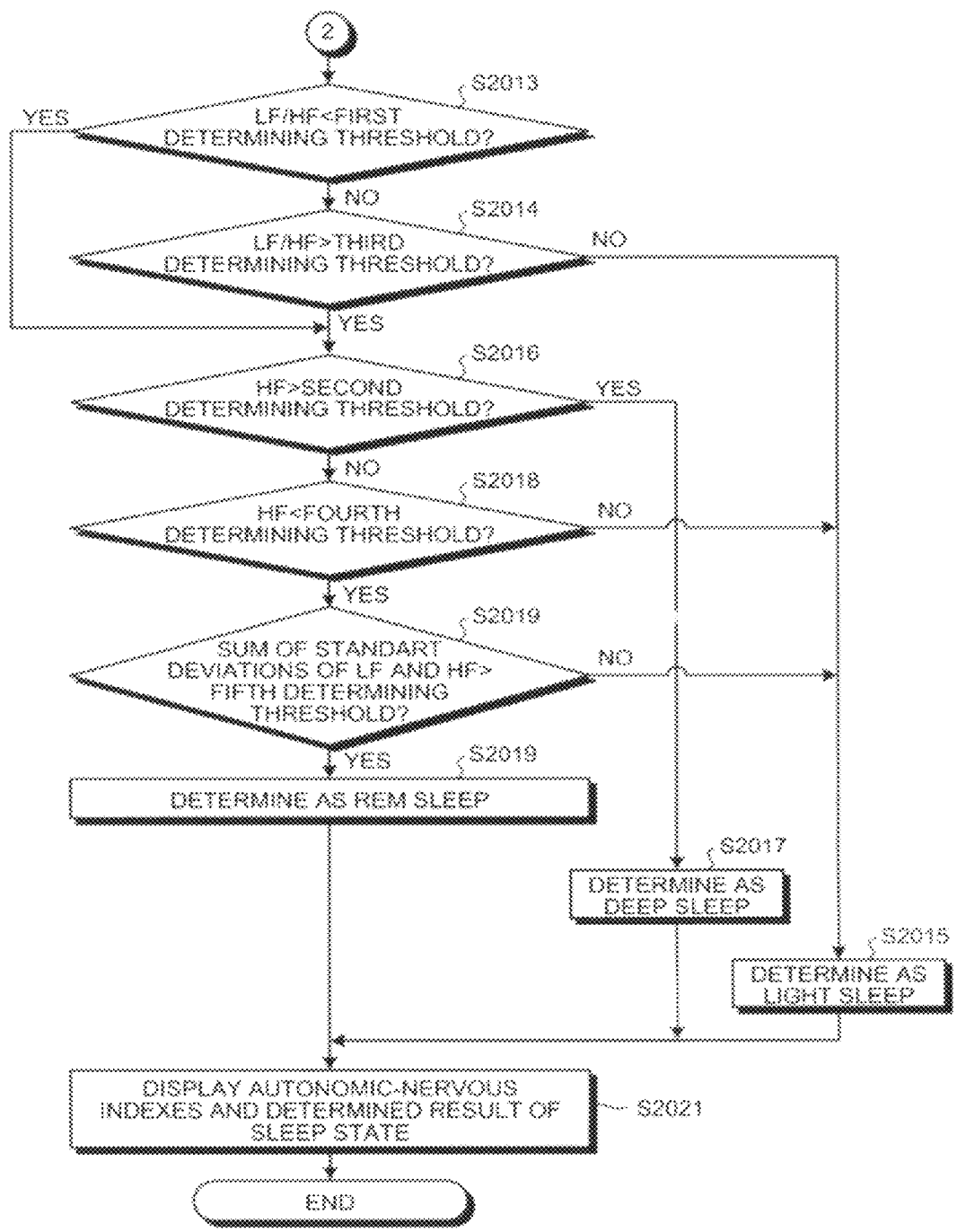

As shown in FIGS. 20A and 20B, in the modification, a process of interpolating the autonomic-nervous indexes (step S2012) is added. A specific method of the interpolating process in the step S2012 is the same as that explained in the first modification in the first embodiment.

Figure 21:
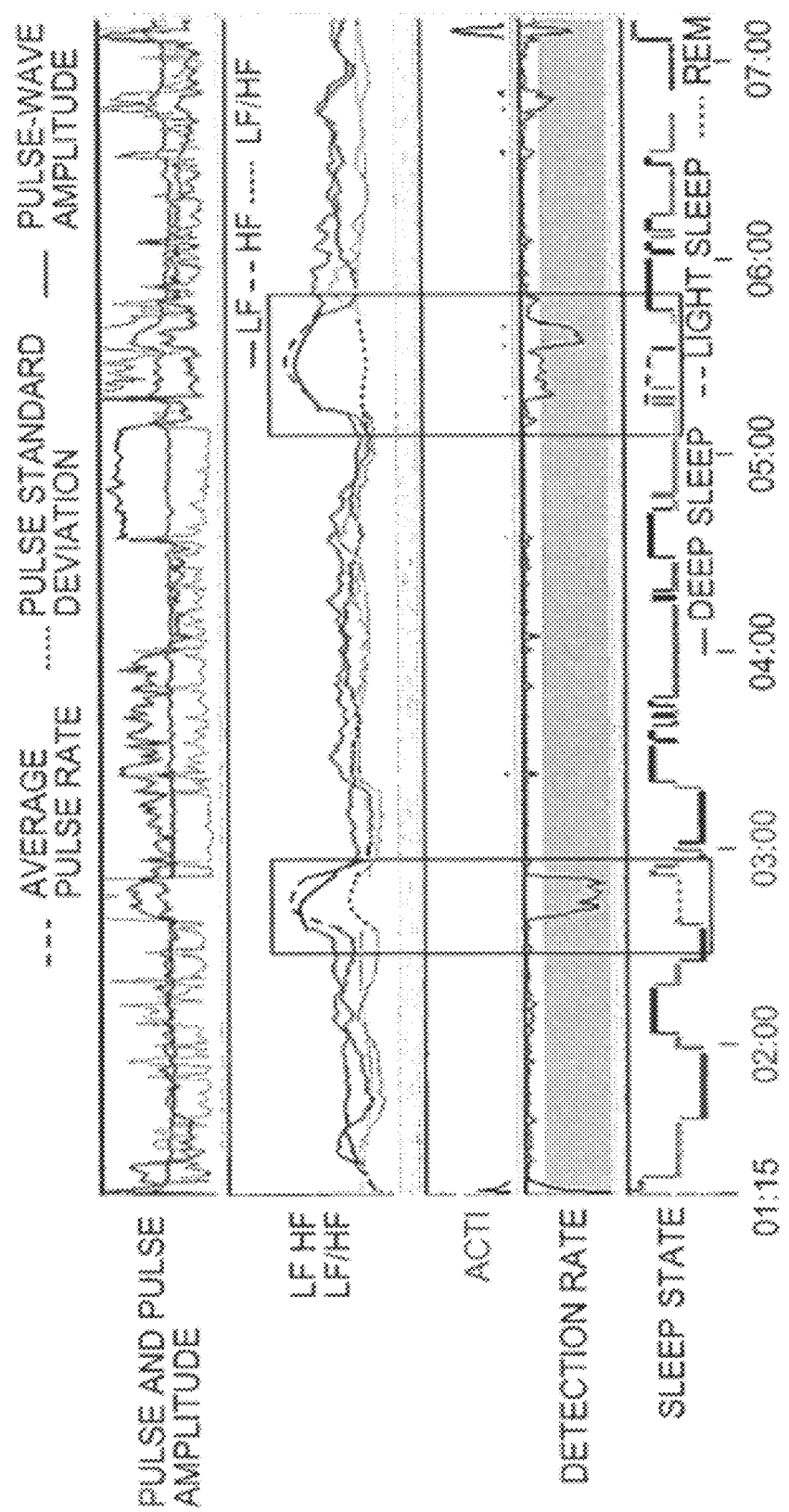
FIG. 21 is a graph representing an analysis result including the sleep state displayed on a displaying unit.

As is apparent from the areas surrounded by the frames in FIG. 21, even when the detection rate is smaller than a predetermined threshold, the autonomic-nervous indexes interpolated by using the autonomic-nervous indexes before and after the time period and the sleep state determined by using the interpolated autonomic-nervous indexes are displayed on the displaying unit 19.

In a second modification of the second embodiment, the sleep state of the time period in which the autonomic-nervous indexes are not calculated is interpolated by using the sleep states determined before and after the time period.

Figure 22A:
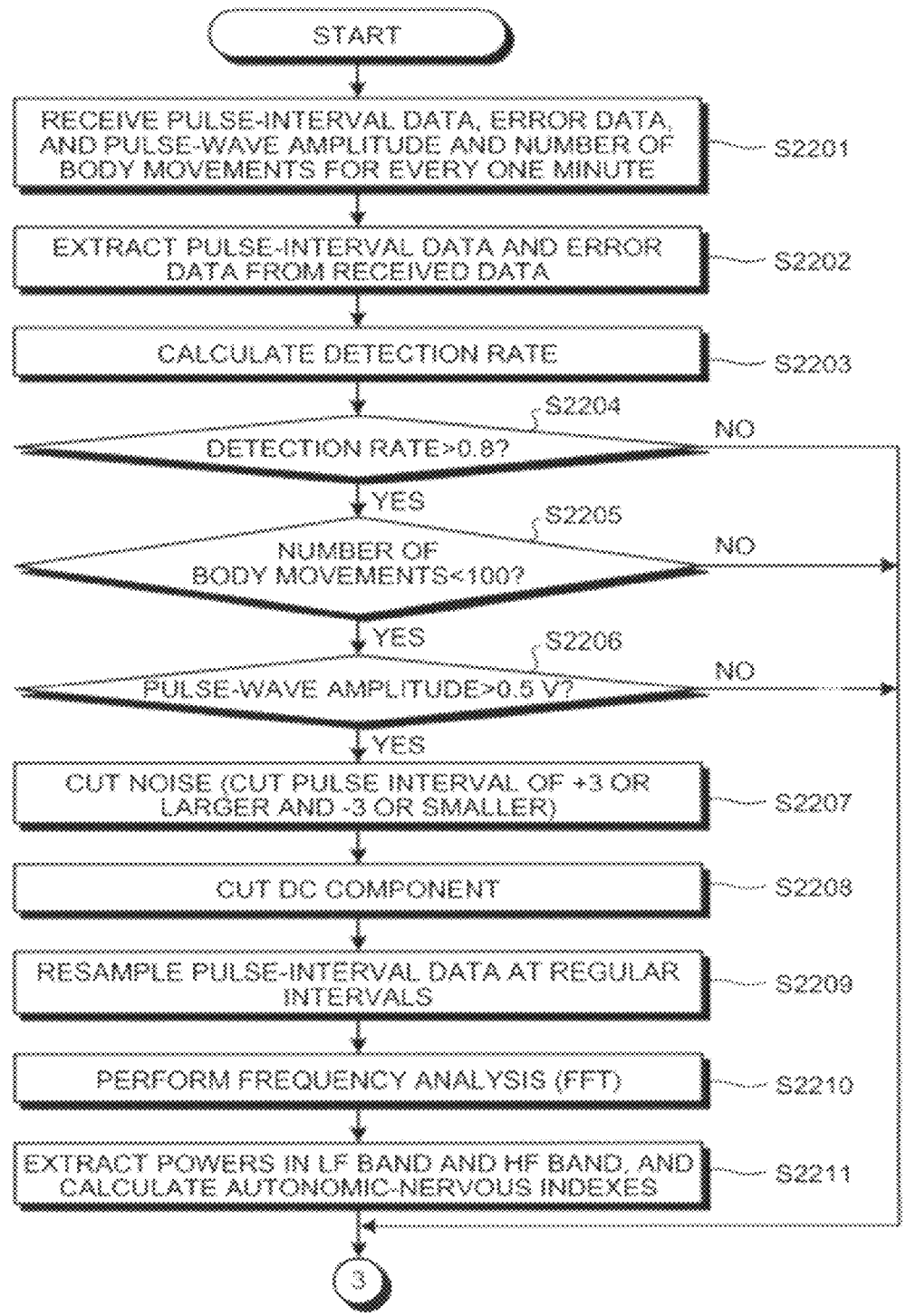
FIG. 22 is a flowchart of a sleep-state determining process according to a second modification of the second embodiment.

As shown in FIGS. 22A and 22B, processes of interpolating the determined result of the sleep state is added as the step S2220 in the sleep-state determining process in the second embodiment shown in FIGS. 18A and 18B.

Figure 23:
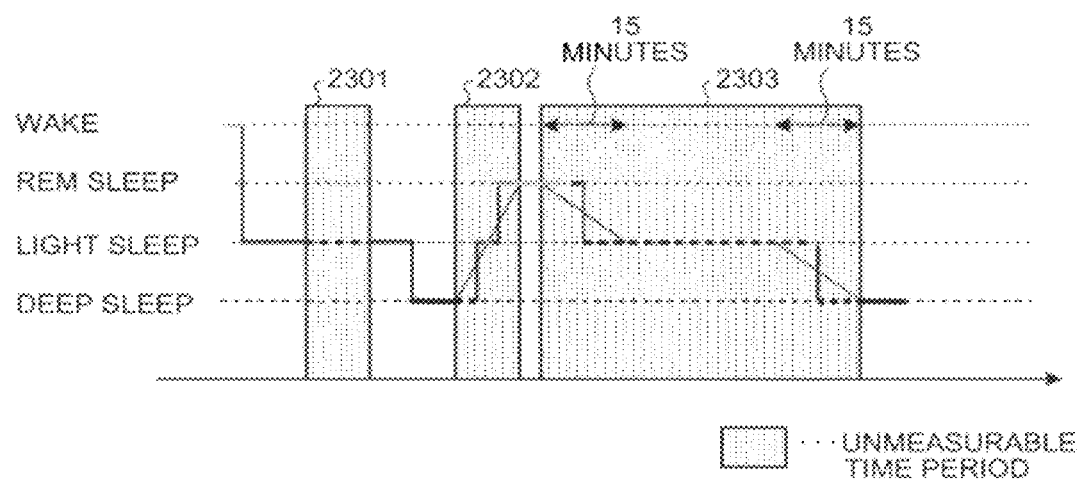
FIG. 23 is a schematic diagram for explaining a sleep-state interpolating method.

FIG. 23 is a schematic diagram for explaining an example of the sleep-state interpolating method in the step S2220. The interpolating method is different depending upon whether the time period in which the autonomic-nervous indexes are not calculated (hereinafter, "an index unmeasurable time period") is shorter than a predetermined time (e.g., 30 minutes). In FIG. 23, the left two time periods 2301 and 2302 are shorter than the predetermined time and the rightmost time period 2303 is not shorter than the predetermined time in the three index unmeasurable time periods.

For the time period 2303, the sleep state is set as the light sleep state excluding predetermined time periods (e.g., 15 minutes each) on both sides of the time period 2303. This is based on the face that generally, the light sleep state has the highest probability to appear. The sleep states of the predetermined time periods on both sides of the time period 2303 are interpolated based on the sleep states before and after the time period 2303 by the following method.

The sleep states of the predetermined time periods on both sides of the time period 2303 and the time periods 2301 and 2302 are each interpolated based on the sleep states determined before and after each time period. If the sleep states before and after the time period are the same, the sleep state same as the sleep states before and after the time period is set for the time period. If the sleep states before and after the time period are not the same, the sleep state satisfying the following two conditions is set for the time period. That is, the sleep state changes in stages from the state before the time period to the state after the time period, and each stage has the same interval in the index unmeasurable time period.

For example, in the time period 2302 in FIG. 23, because the sleep state changes from the deep sleep to the light sleep, the time period 2302 include three stages. Accordingly, the time period 2302 is divided into three stages of the deep sleep, the REM sleep, and the light sleep each having the same interval.

Figure 24:
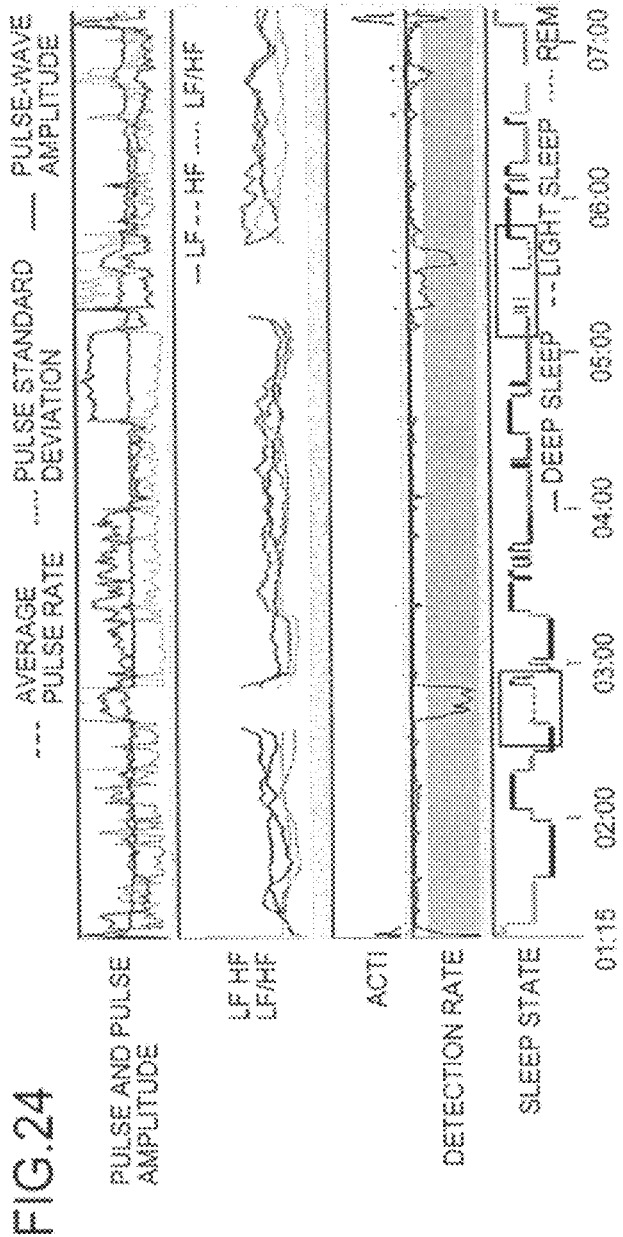
FIG. 24 is a schematic diagram of an analysis result including an interpolated sleep state displayed on a displaying unit.
Figure 25:
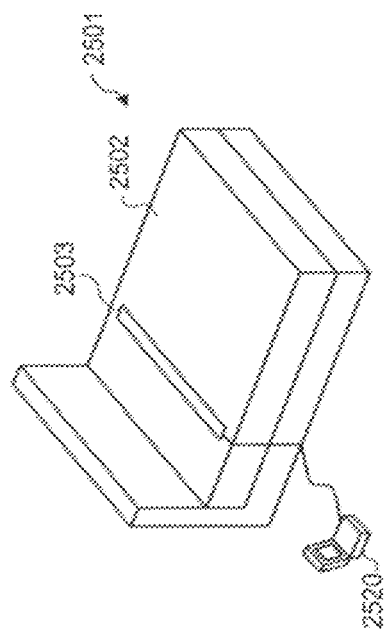
FIG. 25 is a schematic diagram for explaining an arrangement of a mat sensor according to a third embodiment.

As is apparent from the areas surrounded by the frames in FIG. 24, even when the detection rate is smaller than the predetermined threshold, and the autonomic-nervous indexes are not calculated, the sleep state that is interpolated based on the sleep states before and after the time period is displayed on the displaying unit 19.

According to the measuring apparatus of the second embodiment, the sleep state can be determined by using the calculated autonomic-nervous indexes. Furthermore, even when the autonomic-nervous indexes are not calculated for a time period as a result of evaluation of the accuracy of the measured data, the sleep state of the time period can be interpolated based on the sleep states before and after the time period. Thus, the biological information including the sleep state can be monitored with high accuracy.

In the first and second embodiments, the sleep state, the body movement, the autonomic-nervous index, and the like are monitored by using the wearable pulse sensor including the acceleration sensor and the pulse-wave sensor. In a measuring system according to a third embodiment, a mat sensor 2520, which detects a heart rate and the body movement, is used instead of the wearable pulse sensor in the first embodiment.

In the third embodiment, the mat sensor 2520, which is a mat-type sensor module, is used, vibration of a target person's chest or abdomen is monitored by a pressure sensor to detect the heart rate and the body movement during sleeping, and the autonomic-nervous indexes are calculated based on the detected heart rate and body movement in the same manner as those of the above embodiments.

The mat sensor 2520 is connected to a pressure monitoring unit 2503 laid on the surface of a mattress 2502 on a bed 2501.

The pressure monitoring unit 2503 detects presence or absence of the target person and the body movement of the target person. The pressure monitoring unit 2503 is arranged at a position corresponding to the target person's chest or abdomen, and monitors vibration due to the target person's movement. The heart rate and the body movement are detected from the monitored results. In other words, the measuring system according to the third embodiment includes the pressure monitoring unit 2503 instead of the acceleration monitoring unit 26 and the pulse-wave monitoring unit 21 according to the first embodiment.

The pressure monitoring unit 2503 is made of a piezoelectric polymer material such as polyvinylidene fluoride. Specifically, the pressure monitoring unit 2503 is a strip of a piezoelectric element formed by attaching flexible electrode films to both faces of a piezoelectric polymer film.

Figure 26:
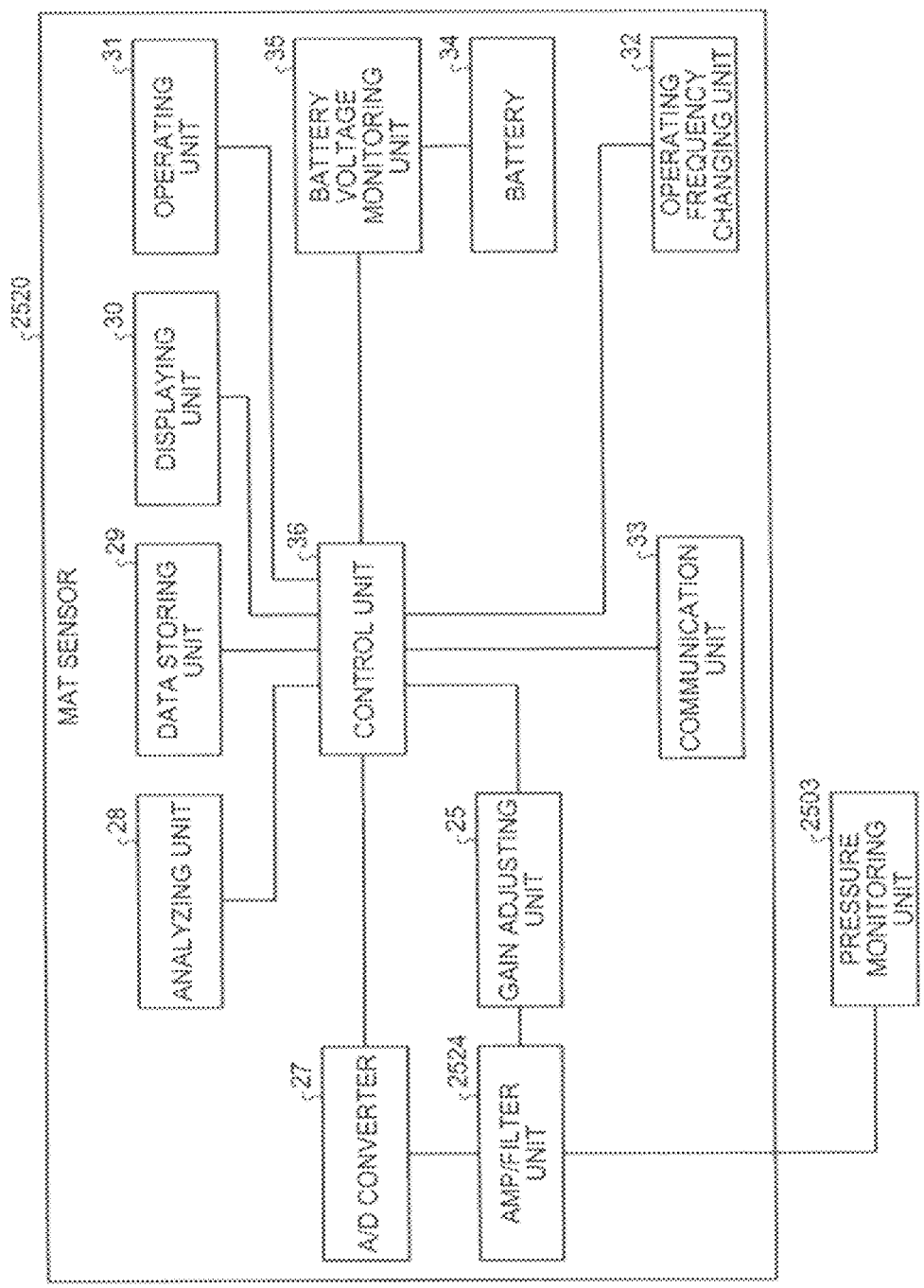
FIG. 26 is a block diagram of the mat sensor.

As shown in FIG. 26, the mat sensor 2520 includes an amp/filter unit 2524, the gain adjusting unit 25, the A/D converter 27, the analyzing unit 28, the data storing unit 29, the displaying unit 30, the operating unit 31, the operating-frequency changing unit 32, the communication unit 33, the battery 34, the battery-voltage monitoring unit 35, and the control unit 36.

The mat sensor 2520 in the third embodiment is different from the pulse sensor 20 in the first embodiment in the following points. That is, in the mat sensor 2520, the acceleration monitoring unit 26 and the pulse-wave monitoring unit 21 are not used, and the pressure monitoring unit 2503 is connected to the amp/filter unit 2524. In addition, the function of the amp/filter unit 2524 is different from the amp/filter unit 24 in the first embodiment. Because configurations and functions of other components are the same as those in FIG. 6 that is a block diagram of the pulse sensor 20 according to the first embodiment, the same reference numerals are given to the components and the explanation thereof is omitted.

The amp/filter unit 2524 separates the output from the pressure monitoring unit 2503 into body movement components and heart rate components, and outputs them to the A/D converter 27. Filters that are suitable for the body-movement monitoring band and the heart-rate monitoring band are used, respectively.

The measuring system according to the third embodiment monitors the heart rate instead of the pulse wave in the first embodiment, and the monitored results are processed similarly to those of the pulse wave in the first embodiment. The monitored results of the heart rate and the pulse wave are substantially the same as data for calculating the autonomic-nervous indexes. The other configurations and processes of the measuring system according to the first embodiment are the same as those of the measuring system according to the first embodiment, and the explanation thereof is omitted.

The measuring apparatus including the mat sensor in the third embodiment can monitor the autonomic-nervous indexes with high accuracy.

Figure 27:
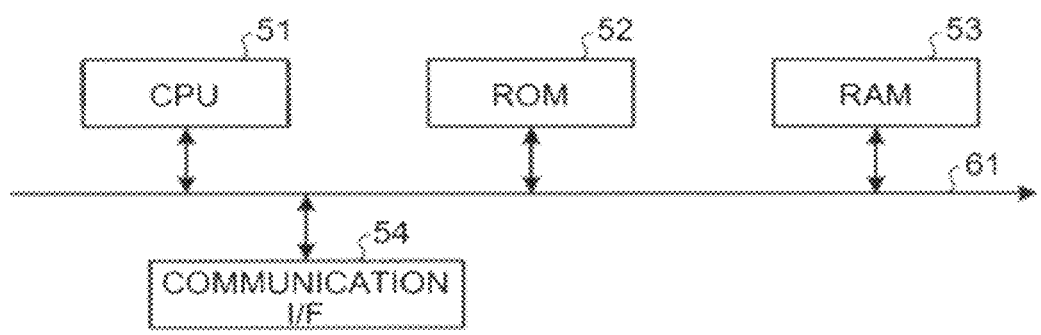
FIG. 27 is a block diagram of a hardware configuration of a measuring apparatus according to the first to third embodiments.

FIG. 27 is a block diagram of a hardware configuration of the measuring apparatus according to the first to third embodiments.

The measuring apparatus according to the first to third embodiments includes a control unit such as a central processing unit (CPU) 51, a storing unit such as a read only memory (ROM) 52 and a random access memory (RAM) 53, a communication interface (communication I/F) 54 for connecting to a network to interact data, an external storing device such as a hard disc drive (HDD) and a compact disc (CD) drive, a display unit, an input unit such as a key board and a mouse, and a bus 61 for connecting the components to each other, that is, the measuring apparatus according to the first to third embodiments has a hardware configuration utilizing a general computer.

An autonomic-nervous index monitoring program executed by the measuring apparatus according to the first to third embodiments is provided, in a form of a file installable or executable on a computer, in a recording medium readable by the computer such as a compact disk read only memory (CD-ROM), a flexible disk (FD), a compact recordable (CD-R), a digital versatile disk (DVD), or the like.

Alternatively, the autonomic-nervous index monitoring program can be stored in a computer connected to the network such as the Internet, and be downloaded to the measuring apparatus via the network. Still alternatively, the autonomic-nervous index monitoring program can be provided or distributed via the network such as the Internet. Still alternatively, the autonomic-nervous index monitoring program can be provided by storing it in a ROM or the like in advance.

The autonomic-nervous index monitoring program executed by the measuring apparatus according to the first to third embodiments includes modules including the above units (the receiving unit, the data extracting unit, the detection-rate calculating unit, and the index calculating unit). In practice, in the hardware, the CPU 51 (processor) reads out the autonomic-nervous index monitoring program from the above recording medium and executes it to load the above units onto a main memory, thereby generating the above units on the main memory.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An apparatus for measuring an autonomic-nervous index, comprising:
   a detection-rate calculating unit that calculates a detection rate representing a ratio of number of interval data generated within a predetermined reference time to a sum of the number of the interval data and number of error data generated within the reference time, the interval data representing a time interval of one cycle of a waveform of at least one of a pulse and a heart rate, the error data representing a content of an error that occurred within the reference time; and
   an index calculating unit that calculates an autonomic-nervous index representing an autonomic-nervous activity state, based on the interval data generated within the reference time, when the detection rate is larger than a first threshold.

2. The apparatus according to claim 1, further comprising a receiving unit that receives the interval data and the error data from a detecting device, the detecting device detecting the waveform of at least one of the pulse and the heart rate of a user and generating the interval data and the error data based on the waveform of the at least one of the pulse and the heart rate, wherein
   the detection-rate calculating unit calculates the number of the interval data and the number of the error data received within the reference time and calculates a ratio of calculated number of the interval data to a sum of the calculated number of the interval data and calculated number of the error data as the detection rate.

3. The apparatus according to claim 1, further comprising:
   a receiving unit that receives the waveform of at least one of the pulse and the heart rate of a user detected by a detecting device, the detecting device detecting the waveform of at least one of the pulse and the heart rate of the user; and
   an analyzing unit that analyzes the waveform of the at least one of the pulse and the heart rate received by the receiving unit for generating the interval data and the error data.

4. The apparatus according to claim 1, wherein the error data includes an out-of-range error representing either that the interval data is smaller than a predetermined second threshold or that the interval data is larger than a predetermined third threshold that is larger than the second threshold.

5. The apparatus according to claim 1, wherein the error data includes a body-movement detected error representing that a body movement of a user is detected when the interval data is generated.

6. The apparatus according to claim 1, wherein the index calculating unit further compares number of body movements of a user detected within the reference time with a predetermined fourth threshold, and calculates the autonomic-nervous index when the number of the body movements is smaller than the fourth threshold.

7. The apparatus according to claim 1, wherein the index calculating unit further compares an average value of an amplitude of the waveform of the interval data in the reference time with a predetermined fifth threshold, and calculates the autonomic-nervous index when the average value is larger than the fifth threshold.

8. The apparatus according to claim 1, wherein the index calculating unit does not calculate the autonomic-nervous index when the detection rate is equal to or smaller than the first threshold.

9. The apparatus according to claim 1, wherein when the detection rate is equal to or smaller than the first threshold, the index calculating unit calculates a first autonomic-nervous index of a first time period in which the detection rate is equal to or smaller than the first threshold by interpolating between a second autonomic-nervous index of a second time period that is right before the first time period and a third autonomic-nervous index of a third time period that is right after the first time period.

10. The apparatus according to claim 1, further comprising a sleep-state determining unit that determines a sleep state of a user including a rapid-eye-movement sleep state, a light sleep state, and a deep sleep, based on a calculated autonomic-nervous index.

11. The apparatus according to claim 10, wherein when the detection rate is equal to or smaller than the first threshold, the sleep-state determining unit determines a first sleep state of a first time period in which the detection rate is equal to or smaller than the first threshold by interpolating between a second sleep state of a second time period that is right before the first time period and a third sleep state of a third time period that is right after the first time period.

12. The apparatus according to claim 11, wherein the sleep-state determining unit compares the first time period with a predetermined sixth threshold, and determines a fourth sleep state of a fourth time period that is obtained by removing predetermined time periods from both sides of the first time period as the light sleep state when the first time period is larger than the sixth time period.

13. A method of measuring an autonomic-nervous index, comprising:
   calculating, using a processor, a detection rate representing a ratio of number of interval data generated within a predetermined reference time to a sum of the number of the interval data and number of error data generated within the reference time, the interval data representing a time interval of one cycle of a waveform of at least one of a pulse and a heart rate, the error data representing a content of an error that occurred within the reference time; and
   calculating, using the processor, including
      comparing the detection rate with a predetermined first threshold, and
      calculating, when the detection rate is larger than the first threshold, an autonomic-nervous index representing an autonomic-nervous activity state, based on the interval data generated within the reference time.

14. A detecting device configured to communicate with an apparatus that measures an autonomic-nervous index representing an autonomic-nerve activity state, the detecting device comprising:
 a detecting unit that detects a waveform of at least one of a pulse and a heart rate of a user;
 an analyzing unit that analyzes the at least one of the pulse and the heart rate of the user detected by the detecting unit, and generates an interval data representing a time interval of one cycle of the waveform of the at least one of the pulse and the heart rate and an error data representing a content of an error occurred when the interval data is generated; and
 a transmission unit that transmits the interval data and the error data to the apparatus.

* * * * *